US010695421B2

(12) United States Patent
Weiner et al.

(10) Patent No.: US 10,695,421 B2
(45) **Date of Patent: *Jun. 30, 2020**

(54) NUCLEIC ACID MOLECULE ENCODING HEPATITIS B VIRUS CORE PROTEIN AND VACCINE COMPRISING THE SAME

(71) Applicant: The Trustees of the University of Pennsylvania, Philadelphia, PA (US)

(72) Inventors: David Weiner, Merion, PA (US); Jian Yan, Wallingford, PA (US); Nyamekye Obeng-Adjei, Lansdowne, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,454

(22) Filed: Feb. 5, 2019

(65) Prior Publication Data

US 2019/0151443 A1 May 23, 2019

Related U.S. Application Data

(63) Continuation of application No. 15/213,747, filed on Jul. 19, 2016, now Pat. No. 10,195,268, which is a continuation of application No. 13/984,771, filed as application No. PCT/US2012/024905 on Feb. 13, 2012, now Pat. No. 9,403,879.

(60) Provisional application No. 61/442,162, filed on Feb. 11, 2011.

(51) Int. Cl.

| | |
|---|---|
| *C07K 14/005* | (2006.01) |
| *C12N 7/00* | (2006.01) |
| *A61K 39/29* | (2006.01) |
| *C07K 14/02* | (2006.01) |
| *A61K 39/12* | (2006.01) |
| *A61P 31/20* | (2006.01) |
| *A61K 39/39* | (2006.01) |
| *A61K 39/00* | (2006.01) |

(52) U.S. Cl.

CPC ............ *A61K 39/292* (2013.01); *A61K 39/12* (2013.01); *A61K 39/39* (2013.01); *A61P 31/20* (2018.01); *C07K 14/005* (2013.01); *C07K 14/02* (2013.01); *C12N 7/00* (2013.01); *A61K 2039/53* (2013.01); *A61K 2039/57* (2013.01); *A61K 2039/572* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| | | | |
|---|---|---|---|
| 4,510,245 | A | 4/1985 | Cousens |
| 4,554,101 | A | 11/1985 | Hopp |
| 4,722,848 | A | 2/1988 | Paoletti |
| 4,790,987 | A | 12/1988 | Compans |
| 4,797,368 | A | 1/1989 | Carter |
| 4,920,209 | A | 4/1990 | Davis |
| 4,945,050 | A | 7/1990 | Sanford |
| 5,017,487 | A | 5/1991 | Stunnenberg |
| 5,036,006 | A | 7/1991 | Sanford |
| 5,077,044 | A | 12/1991 | Stocker |
| 5,110,587 | A | 5/1992 | Paoletti |
| 5,112,749 | A | 5/1992 | Brey, III |
| 5,174,993 | A | 12/1992 | Paoletti |
| 5,223,424 | A | 6/1993 | Cochran |
| 5,225,336 | A | 7/1993 | Paoletti |
| 5,240,703 | A | 8/1993 | Cochran |
| 5,242,829 | A | 9/1993 | Panicali |
| 5,273,525 | A | 12/1993 | Hofmann |
| 5,294,441 | A | 3/1994 | Curtiss, III |
| 5,294,548 | A | 3/1994 | McLinden |
| 5,310,668 | A | 5/1994 | Ellis |
| 5,387,744 | A | 2/1995 | Curtiss, III |
| 5,389,368 | A | 2/1995 | Curtiss, III |
| 5,424,065 | A | 6/1995 | Curtiss, III |
| 5,451,499 | A | 9/1995 | Cochran |
| 5,453,364 | A | 9/1995 | Paoletti |
| 5,462,734 | A | 10/1995 | Letchworth, III |
| 5,407,073 | A | 11/1995 | Sondermeijer |
| 5,470,734 | A | 11/1995 | Sondermeijer |
| 5,474,935 | A | 12/1995 | Chatterjee |
| 5,482,713 | A | 1/1996 | Paoletti |
| 5,580,859 | A | 12/1996 | Felgner |
| 5,591,439 | A | 1/1997 | Plotkin |
| 5,593,972 | A | 1/1997 | Weiner |
| 5,643,579 | A | 7/1997 | Hung |

(Continued)

FOREIGN PATENT DOCUMENTS

| | | | |
|---|---|---|---|
| WO | 9324640 | A2 | 12/1993 |
| WO | 9416737 | A1 | 8/1994 |

(Continued)

OTHER PUBLICATIONS

Negi et al. (Accession No. ADH82159, Mar. 2010).*

(Continued)

*Primary Examiner* — Agnieszka Boesen

(74) *Attorney, Agent, or Firm* — Riverside Law LLP

(57) ABSTRACT

Provided herein are nucleic acid sequences that encode novel consensus amino acid sequences of HBV core protein, as well as genetic constructs/vectors and vaccines that express said protein sequences. Also provided herein are methods for generating an immune response against HBV using the nucleic acid sequences that are provided.

9 Claims, 25 Drawing Sheets

Specification includes a Sequence Listing.

(56) References Cited

U.S. PATENT DOCUMENTS

| | | | |
|---|---|---|---|
| 5,650,309 | A | 7/1997 | Wong-Staal |
| 5,676,594 | A | 10/1997 | Joosten |
| 5,698,202 | A | 12/1997 | Ertl |
| 5,703,055 | A | 12/1997 | Felgner |
| 5,739,118 | A | 4/1998 | Carrano |
| 5,817,637 | A | 10/1998 | Weiner |
| 5,830,876 | A | 11/1998 | Weiner |
| 5,955,088 | A | 9/1999 | Ghiasi |
| 5,962,428 | A | 10/1999 | Carrano |
| 5,981,505 | A | 11/1999 | Weiner |
| 6,034,298 | A | 3/2000 | Lam |
| 6,042,836 | A | 3/2000 | Berman |
| 6,110,161 | A | 8/2000 | Mathiesen |
| 6,156,319 | A | 12/2000 | Cohen |
| 6,261,281 | B1 | 7/2001 | Mathiesen |
| 6,589,529 | B1 | 7/2003 | Choi |
| 6,697,669 | B2 | 2/2004 | Dev |
| 6,939,862 | B2 | 9/2005 | Bureau |
| 6,958,060 | B2 | 10/2005 | Mathiesen |
| 7,238,522 | B2 | 7/2007 | Hebel |
| 7,245,963 | B2 | 7/2007 | Draghia-Akli |
| 7,328,064 | B2 | 2/2008 | Mathiesen |
| 7,964,196 | B2 * | 6/2011 | de los Rios .......... A61K 9/5184 424/189.1 |
| 8,298,820 | B2 | 10/2012 | Weiner |
| 9,238,679 | B2 | 1/2016 | Weiner |
| 9,403,879 | B2 | 8/2016 | Weiner |
| 2003/0099668 | A1 * | 5/2003 | Bachmann ............. A61K 39/00 424/204.1 |
| 2004/0146529 | A1 | 7/2004 | Selby |
| 2004/0156863 | A1 | 8/2004 | Page |
| 2004/0175724 | A1 | 9/2004 | Draghia-Akli |
| 2004/0175727 | A1 | 9/2004 | Draghia-Akli |
| 2005/0005263 | A1 | 1/2005 | Miyazaki |
| 2005/0052630 | A1 | 3/2005 | Smith |
| 2005/0129712 | A1 | 6/2005 | Reimann |
| 2009/0004716 | A1 | 1/2009 | Draghia-Akli |
| 2009/0214593 | A1 | 8/2009 | Sallberg |
| 2010/0291144 | A1 | 11/2010 | Ramanathan |
| 2011/0293726 | A1 | 12/2011 | De |
| 2012/0034256 | A1 | 2/2012 | Weiner |

FOREIGN PATENT DOCUMENTS

| | | |
|---|---|---|
| WO | 1998012332 | 3/1998 |
| WO | 0026385 A1 | 5/2000 |
| WO | 2001085208 | 11/2001 |
| WO | 0214478 A2 | 2/2002 |
| WO | 2004026899 A1 | 4/2004 |
| WO | 2005000235 A2 | 1/2005 |
| WO | 2005023293 A1 | 3/2005 |
| WO | 2005116270 A2 | 12/2005 |
| WO | 2006033679 A2 | 3/2006 |
| WO | 1832956 A | 9/2006 |
| WO | 2008089144 A2 | 7/2008 |
| WO | 2008093976 A1 | 8/2008 |
| WO | 2008103380 A2 | 8/2008 |
| WO | 2009036228 A2 | 3/2009 |
| WO | 2009073330 A2 | 6/2009 |
| WO | 101502650 A | 8/2009 |
| WO | 2009124312 A2 | 10/2009 |
| WO | 2009130588 A2 | 10/2009 |
| WO | 2010016071 A2 | 2/2010 |
| WO | 2010057159 A2 | 5/2010 |
| WO | 2010127115 A1 | 11/2010 |
| WO | 2827080 A1 | 8/2012 |
| WO | 2012109404 A1 | 8/2012 |
| WO | 2012109668 A1 | 8/2012 |
| WO | 94016737 | 10/2012 |
| WO | 2882839 A1 | 3/2014 |
| WO | 2014047286 A1 | 3/2014 |

OTHER PUBLICATIONS

Shahrokhi et al., "Priming Hepatitis B Surface (HBsAg)- and Core Antigen (HBcAg)-Specific Immune Responses by Chimeric, HBcAg with a HBsAG "a" Determinant," Iranian Biomedical Journal, 2006, 10(2):61-68.

Xing et al., 'Novel DNA vaccine based on hepatitis B virus core gene induces specific immune responses in Balb/c mice,' World J Gastroenterol, 2005, 11(29):4583-4586.

Abdulhaqq et al., "DNA vaccines: developing new strategies to enhance immune responses," Immunol Res, 2008, 42:219-232.

Whitacre et al., 'Use of hepadnavirus core proteins as vaccine platforms,' Expert Reviews, 2009, 8(11):1565-1573.

Yang et al.,Induction of potent Th1-type immune responses from a novel DNA vaccine for West Nile virus New York isolate (WNV-NY1999). J Infect Dis. 184(7):809-16, 2001.

Frelin, L., et al., 'Codon optimization and mRNA amplification effectively enhances the immunogenicity of the hepatitis C virus nonstructural 3/4A gene.' Gene Ther, 2004, 11(6): 522-533.

Hirao, L.A. et al., 'Intradermal subcutaneous immunization by electroporation improves plasmid vaccines delivery and potency in pigs and rhesus macaques', Vaccine, 2008, 26(3):440-448.

Luckay A, et al., 'Effect of plasmid DNA vaccine design and in vivo electroporation on the resulting vaccine-specific immune responses in rhesus macaques', J. Virol, 2007, 81(10):5257-69.

Ahlen, G. et al., 'In vivo electroporation enhances the immunogenicity of hepatitis C virus nonstructural 3/4A DNA by increased local DNA uptake, protein expression, inflammation, and infiltration of CD3+T cells', J Immunol, 2007, 179:4741-4753.

Yan, J. et al., 'Enhanced cellular immune responses elicited by an engineered HIV-1 subtype B consensus-based envelope DNA vaccine', Mol Ther, 2007, 15(2):411-421.

Rolland et al., 'Reconstruction and function of ancestral center-of-tree human immunodeficiency virus type 1 proteins,' J. Virol., 2007, 81(16):8507-14.

Kyte et al., 'A simple method for displaying the hydropathic character of a protein,' J. Mol. Biol., 1982, 157(1):105-32.

Chisari et al., 'Rous-Whipple Aware Lecture. Viruses, immunity, and cancer: lessons from hepatitis B,' Am J Pathol, 2000, 156(4):1117-32.

Pumpens et al., 'HBV core particles as a carrier for B cell/T cell epitopes,' Intervirology, 2001, 44(2-3):98-114.

Deny et al., 'Hepatitis B virus: from diagnosis to treatment,' Pathol Biol (Paris), 2010, 54(4):245-53.

Michel et al., 'Hepatitis B vaccines: protective efficacy and therapeutic potential,' Pathol Biol (Paris), 2010, 58(4):288-95.

Q6VBP1, UniProtKB/TrEMBL entry Q6VBP.sub.—1HBV. Retrieved from the internet <URL: http://www.uniprot.org/uniprot/Q6VBP1.txt?version=54>.

GeneBank Accession No. JF439753, Hepatitis B virus isolate MAU95A2 polymerase (p) gene, complete cds. Retrieved from the internet <URL:http:www.ncbi.nlm.nih.gov/nuccore/JF439753>.

Negal GeneBank: ADH82159.1, Hepatitis B virus core protein, 2010, 2 pages.

Yin et al., "Hepatitis B virus core protein as an epitope vaccine carrier", Chinese J of Biotech, 26(4): 431-438,2010.

Sendi et al., 'CTL escape mutations of core protein are more frequent in strains of HBeAg negative patients with low levels of HBV DNA,' J Clin Virol., 2009, 46(3):259-264.

Supplementary European Search Report for EP 12744961.9, dated Jun. 5, 2015. 10 pages.

EA Office Action for EA201590597 dated Sep. 14, 2018, 13 pages.

GeneBank Accession No. ACT21915.1, dated Nov. 1,2010; https://www.ncbi.nlm.nih.gov/protein/ACT21915.1, 1 page.

GeneBank Accession No. ACT21908.1, dated Nov. 1,2010; https://www.ncbi.nlm.nih.gov/protein/ACT21908.1, 1 page.

GeneBank Accession No. ACP20705.1, dated Jul. 8, 2009; https://www.ncbi.nlm.nih.gov/protein/ACP20705.1, 1 page.

GeneBank Accession No. ACB69749.1, dated Apr. 8, 2008; https://www.ncbi.nlm.nih.gov/protein/ACB69749.1, 1 page.

GeneBank Accession No. ABU84854.1, dated Feb. 25, 2008; https://www.ncbi.nlm.nih.gov/protein/ABU84854.1, 1 page.

GeneBank Accession No. ABN64126.1, dated Nov. 28, 2008; https://www.ncbi.nlm.nih.gov/protein/ABN64126.1, 1 page.

(56) References Cited

OTHER PUBLICATIONS

GeneBank Accession No. CAM58593.1, dated Jan. 8, 2008; https://www.ncbi.nlm.nih.gov/protein/CAM58593.1, 1 page.
Bartholomeusz et al., (2004) "Hepatitis B virus genotypes: comparison of genotyping methods", Rev Med Virol, 14(1): pp. 3-16.
Nystrom et al., "Improving on the Ability of Endogenous Hepatitis B Core Antigen to Prime Cytotoxic T Lymphocytes", UID, 201(12):1867-1879, 2010.
Office Action dated Jan. 16, 2018 for U.S. Appl. No. 15/213,747 (pp. 1-12).
Office Action dated Jun. 6, 2018 for U.S. Appl. No. 15/213,747 (pp. 1-9).
Notice of Allowance dated Sep. 21, 2018 for U.S. Appl. No. 15/213,747 (pp. 1-5).
Corrected Notice of Allowability dated Oct. 30, 2018 for U.S. Appl. No. 15/213,747 (pp. 1-2).
Notice of Allowability dated Nov. 28, 2018 for U.S. Appl. No. 15/213,747 (pp. 1-2).
Obeng-Adjei N, 'Investigating and Manipulating Immune Responses to Hepatotropic Pathogens Using Synthetic DNA', University of Pennsylvania, Publicly Accessible Penn Dissertations, Paper 679, (Jan. 1, 2013), URL: http://repository.upenn.edu/cgi/viewcontent.cgi?article=1837&c, 101 pages.
Sullivan et al., "CD8+ cellular immunity mediates rAd5 vaccine protection against Ebola virus infection of nonhuman primates" 2011, Nat Med 17: 1128-1131.
Ge et al., 2012, 'Removing N-Terminal Sequences in Pre-S1 Domain Enhanced Antibody and B-Cell Responses by an HBV Large Surface Antigen DNA Vaccine', PLoS One, vol. 7, Issue 7, pp. 1-9 (e41573).
Araujo et al., 2009, "Expression of Hepatitis B Virus Surface Antigen (HBsAg) from Genotypes A, D and F and Influence of Amino Acid Variations Related or Not to Genotypes on HBsAg Detection", Brazilian Journal of Infectious Diseases, vol. 13, No. 4, pp. 266-271.
Michele A. Kutzler et al., 'DNA vaccines: ready for prime time?,' Nat Rev Gen, 2008, 9:776-788.
Chen et al., 2011, "Enhanced Effect of DNA Immunization plus in Vivo Electroporation with a Combination of Hepatitis B Virus Core-PreS1 and S-PreS1 Plasmids", Clinical and Vaccine Immunology, vol. 18, No. 11, pp. 1789-1795.
Obeng-Adjei et al., 2013, "DNA vaccine cocktail expressing genotype A and C HBV surface and consensus core antigens generates robust cytotoxic and antibody responses in mice and Rhesus macaques", Cancer Gene Therapy, vol. 20, pp. 652-662.
Canadian Office Action for Application No. 2,827,080, dated Apr. 18, 2019, 4 pages.
Eurasian Office Action (with English language translation) for Application No. 201590597, dated May 13, 2019, 12 pages.
European Patent Office Communication pursuant to Article 94(3) EPC for Application No. 13839650.2, dated Jul. 12, 2019, 10 pages.
EA Office Action (with English language translation) for Application No. 201892795, dated Jul. 17, 2019, 6 pages.
Canadian Examination Search Report for Application No. CA2,882,839, dated Jul. 11, 2019, 3 pages.

* cited by examiner

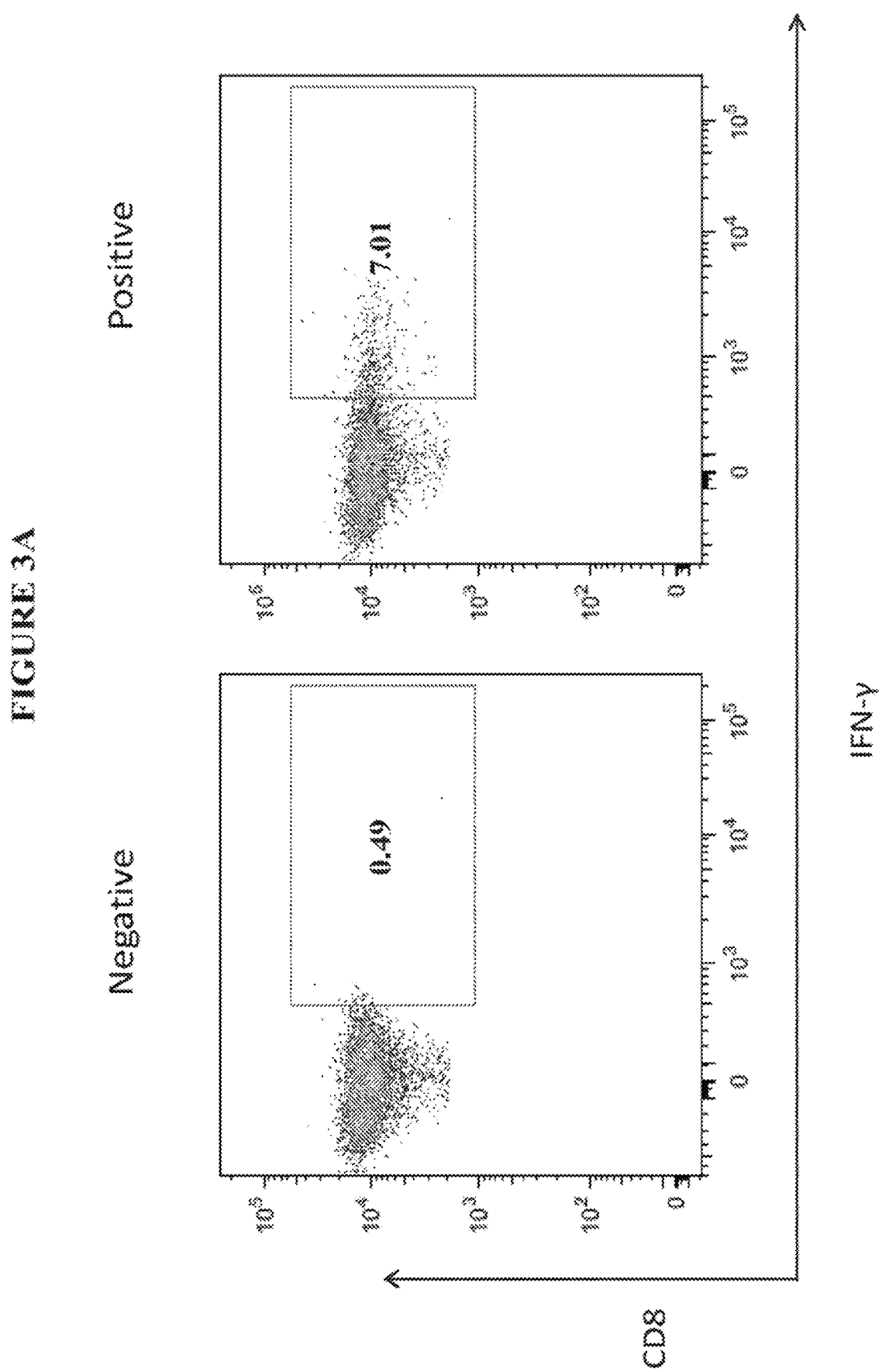

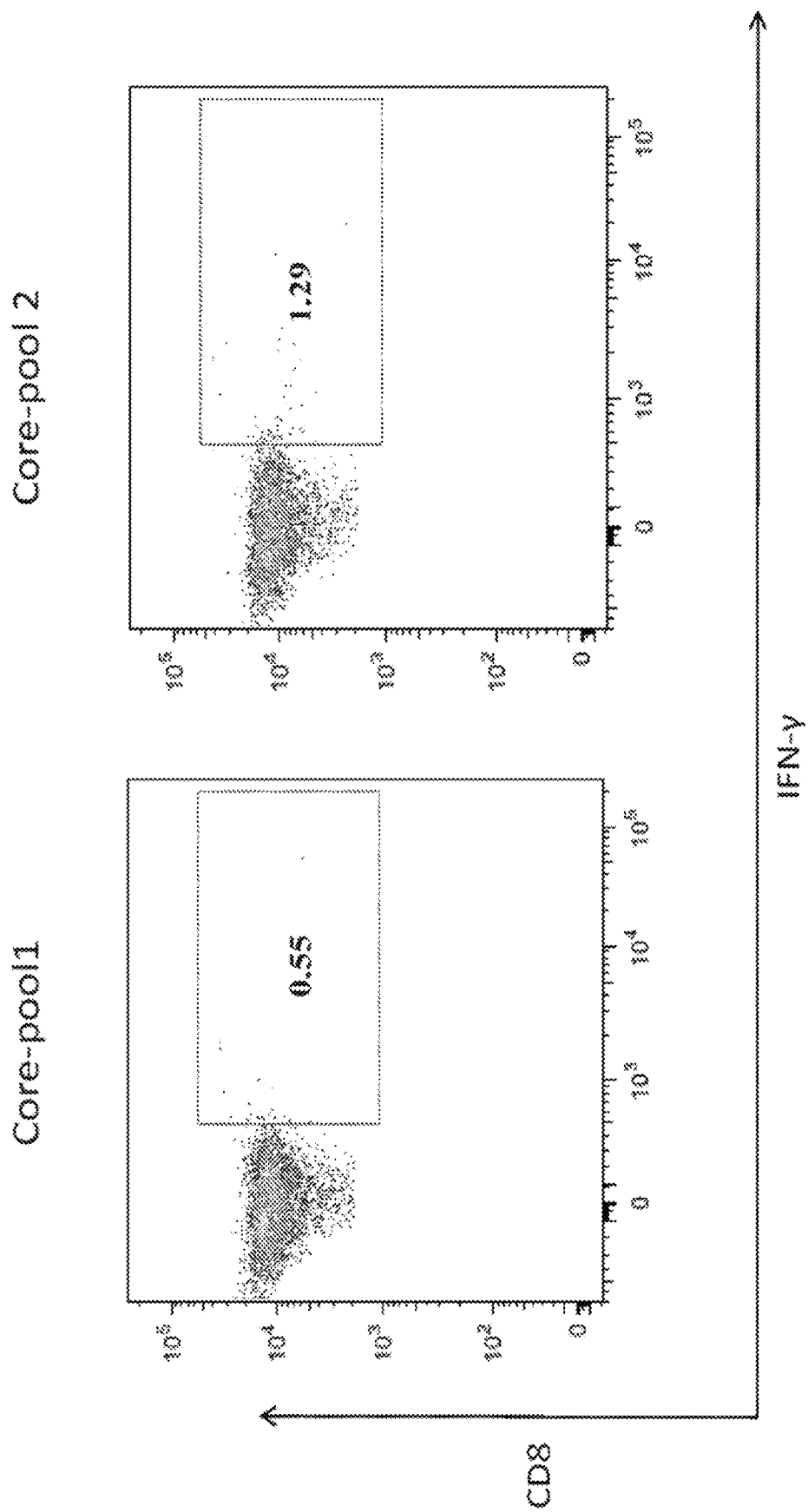

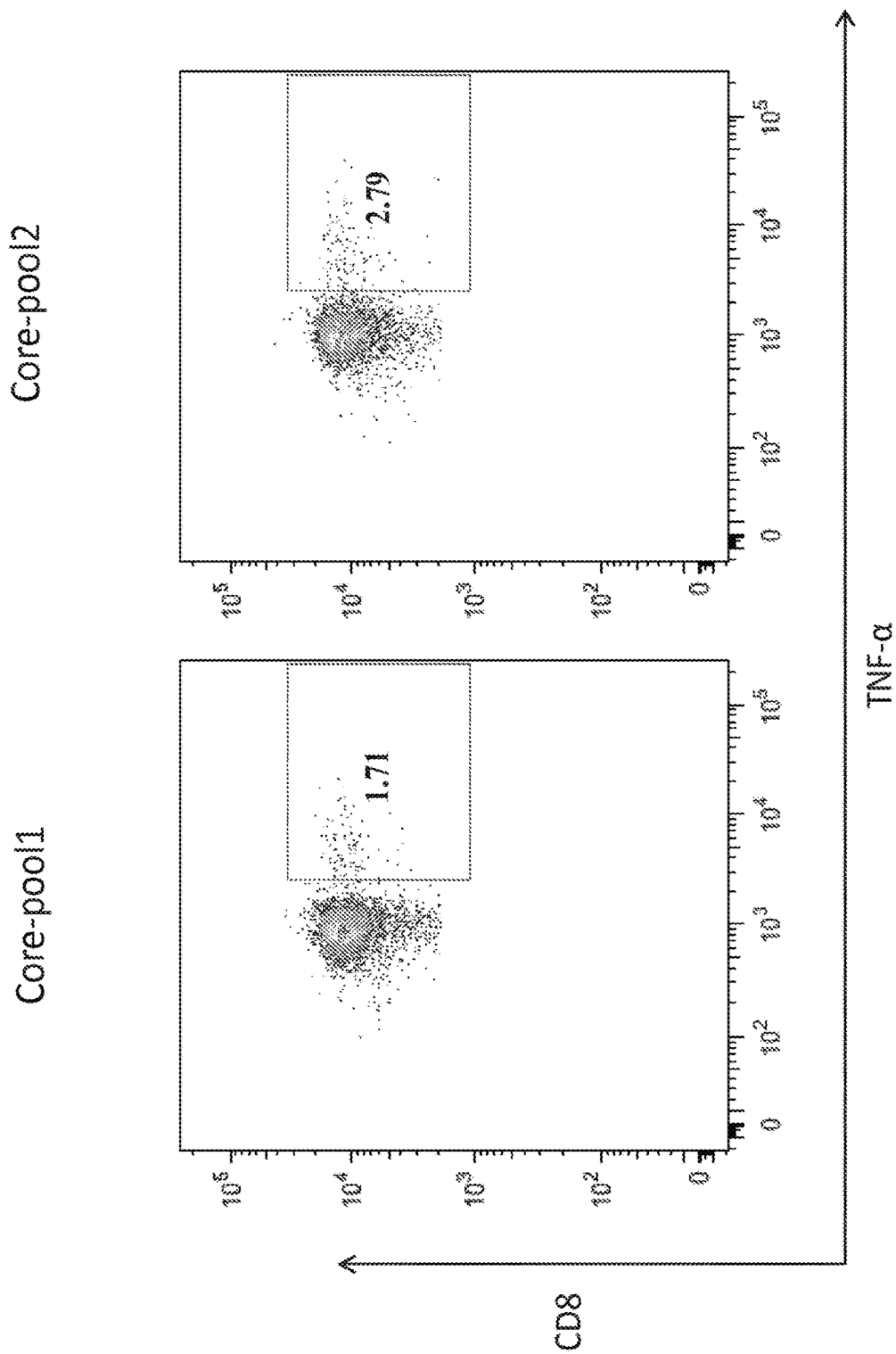
FIGURE 4A, continued

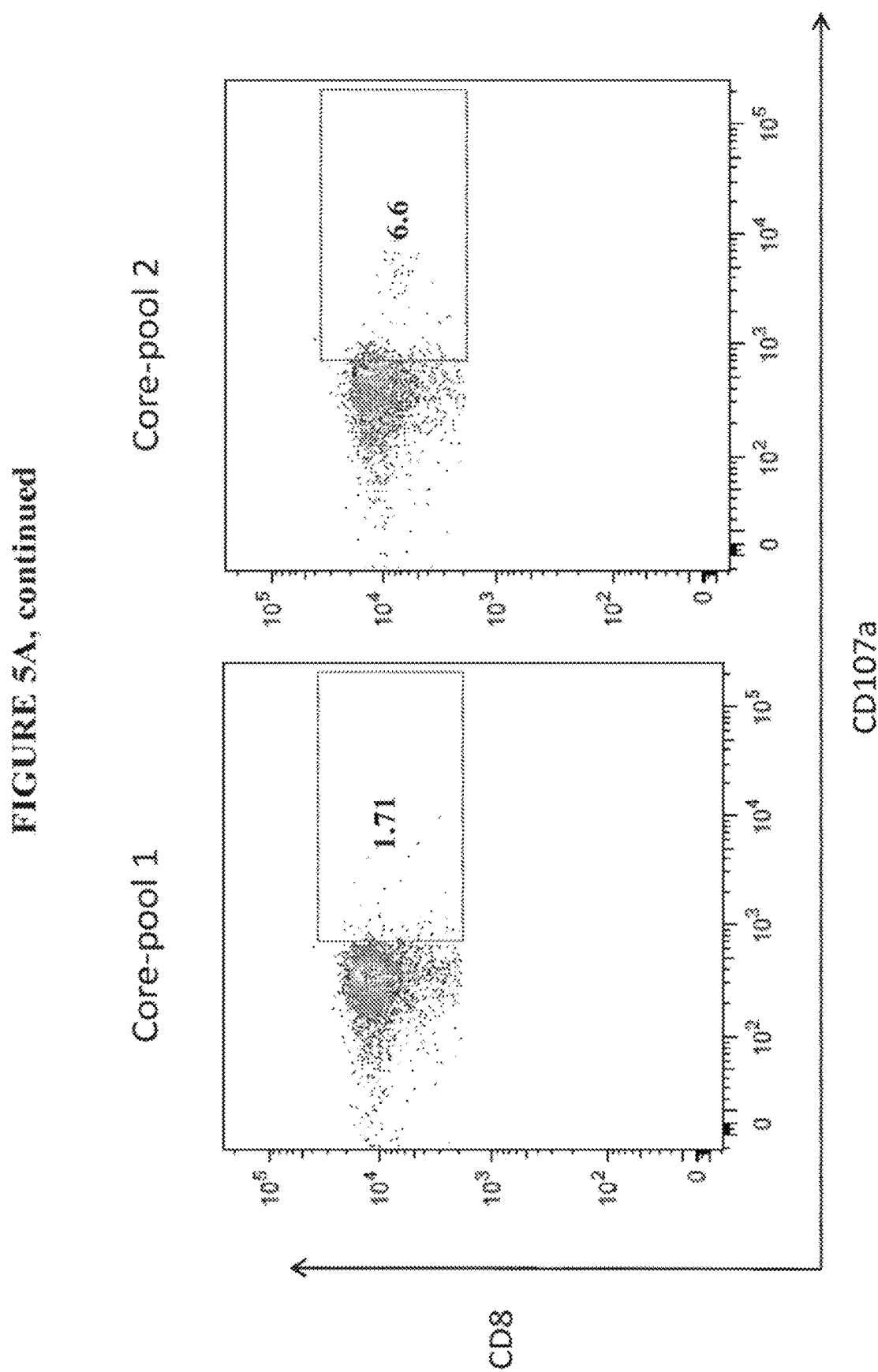

pVAX

FIGURE 6A, continued
pMCore
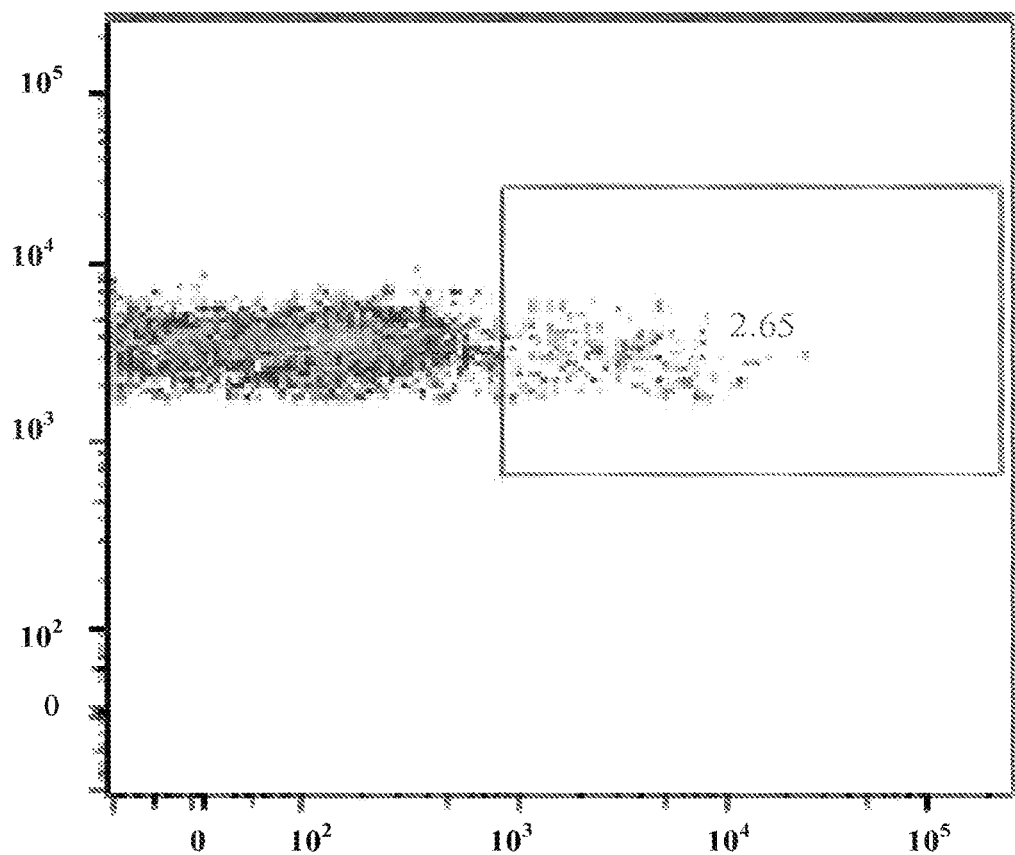

FIGURE 6A, continued
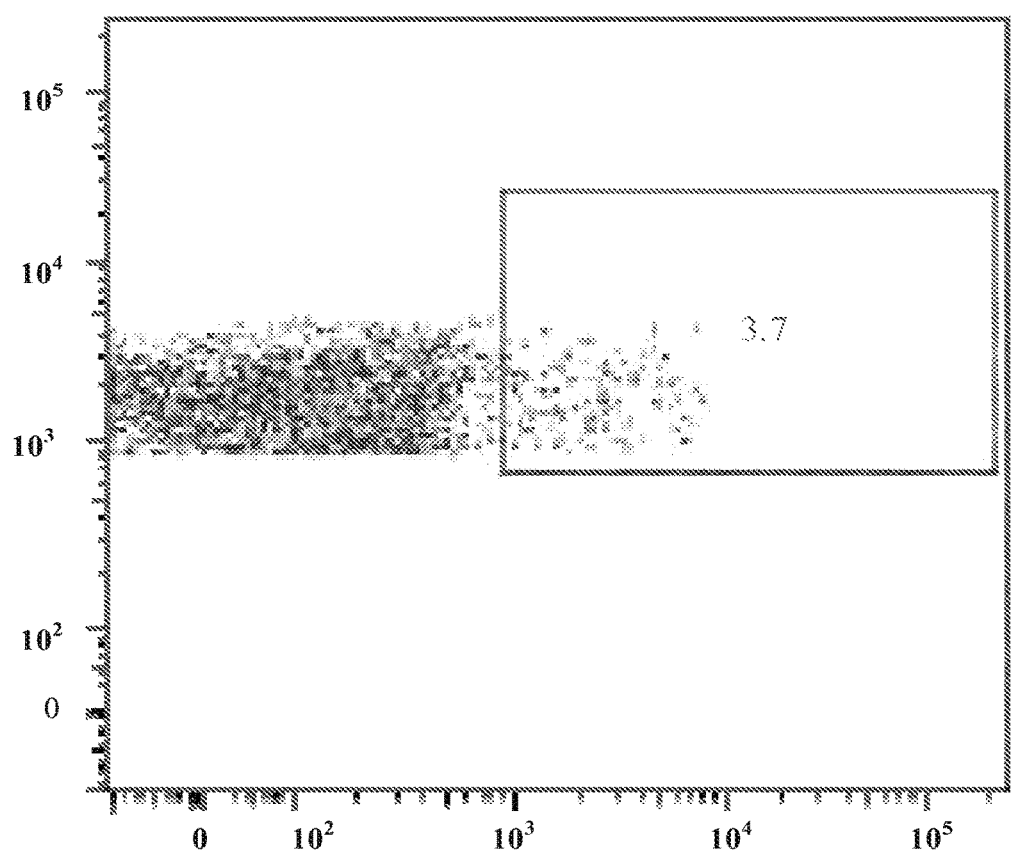

FIGURE 7A, continued
pMCore
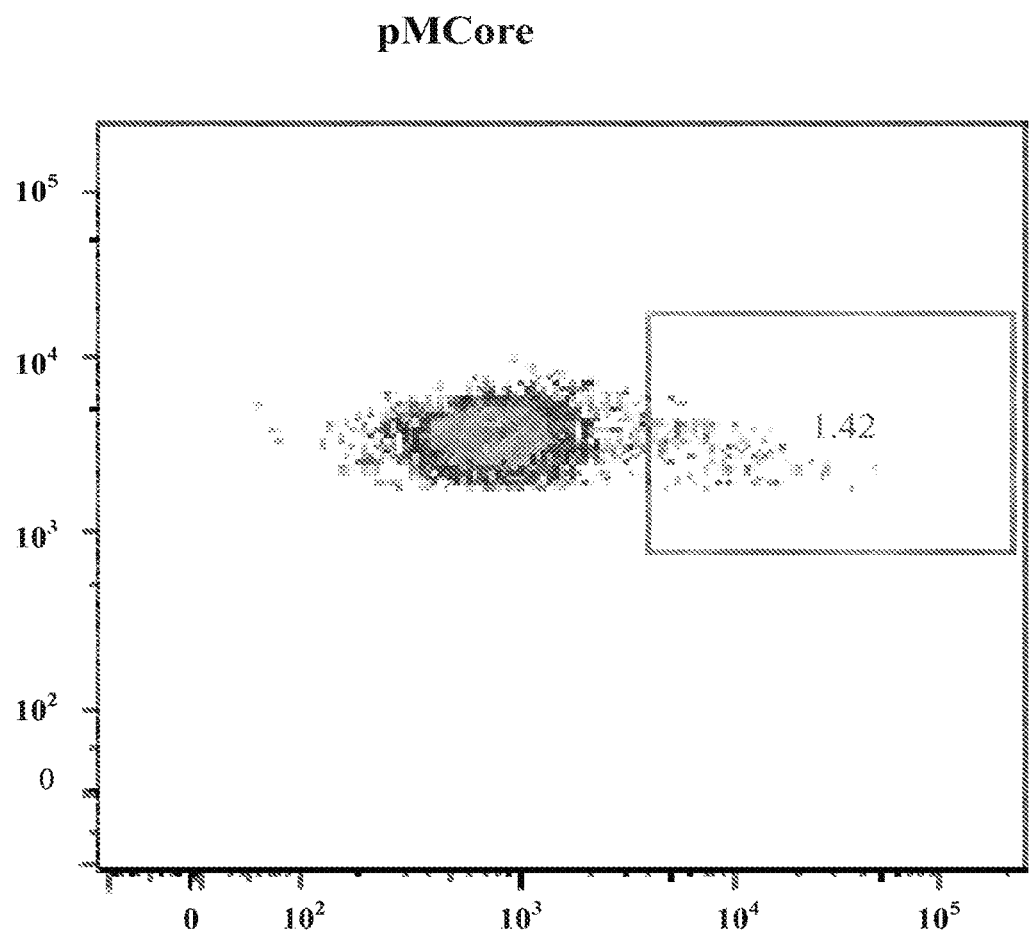

FIGURE 7A, continued
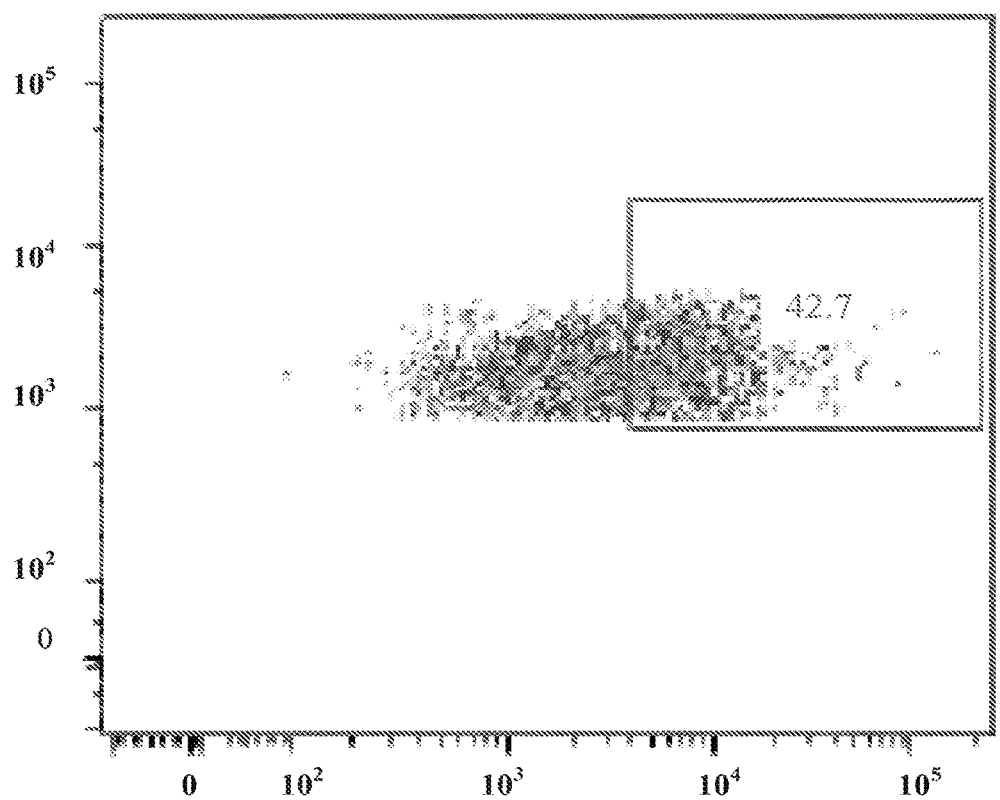

NUCLEIC ACID MOLECULE ENCODING HEPATITIS B VIRUS CORE PROTEIN AND VACCINE COMPRISING THE SAME

CROSS-REFERENCE TO RELATED APPLICATIONS

This application is a continuation of U.S. patent application Ser. No. 15/213,747, filed Jul. 19, 2016, which is a continuation of U.S. patent application Ser. No. 13/984,771, filed Oct. 7, 2013, which is the U.S. national phase application filed under 35 U.S.C. § 371 claiming benefit to International Patent Application No. PCT/US12/024905, filed Feb. 13, 2012, which is entitled to priority under 35 U.S.C § 119(e) to U.S. Provisional Patent Application No. 61/442,162, filed Feb. 11, 2011, each of which applications are incorporated by reference herein in their entireties.

FIELD OF THE INVENTION

The present invention relates to nucleic acid sequences encoding hepatitis B virus (HBV) core proteins and fragments thereof; to hepatitis B virus (HBV) core proteins and fragments thereof, to improved HBV vaccines, improved methods for inducing immune responses against HBV, and improved methods for prophylactically and/or therapeutically immunizing individuals against HBV.

BACKGROUND OF THE INVENTION

This application claims priority to U.S. Provisional Patent Application No. 61/442,162, filed on Feb. 11, 2011, which is incorporated herein by reference.

Hepatitis B is a common infection prevalent across the globe that leads to the development of cirrhosis, liver failure, and hepatocellular carcinoma. A significant number of hepatitis cases go unreported due to the asymptomatic nature of the disease. Nevertheless, about 350 million chronic Hepatitis B cases are reported every year. Most of the hepatitis infected population is in underdeveloped or developing countries.

The virus is divided into four major serotypes (adr, adw, ayr, ayw) based on antigenic epitopes present on its envelope proteins. There are at least eight genotypes (A-H) of HBV according to variation of the genomic sequences. The alternative genotypes of HBV have prevalent geographic distribution.

Table 1 the geographic distribution of HBV genotypes.

TABLE 1

Geographic Distribution of HBV

| HBV genotype | HBV genosubtype | HBsAg subtype | Frequency | Main geographical distribution |
| --- | --- | --- | --- | --- |
| A | A2 | adw2 | High | Europe, North America, Australia |
|   | A1 | ayw1, adw2 | High | Africa |
| B | B1 B2, B3 | adw2 | High | Far East |
|   | B4 | ayw1 | High | Far East |
|   | B2 | adw3 | Low | Far East |
| C | C1, C2, C4 | adr | High | Far East |
|   | C3 | adrq- | High | New Guinea., Pacific |
|   | C1, C2 | ayr | High | Far East |
|   | C1, C3 | adw2 | Low | Far East |
|   | C4 | ayw3 | Low | Far East, Pacific |
| D | D1, D3, D4 | ayw2 | High | West Asia, Eastern Europe, Mediterranean |
|   | D2, D3 | ayw3 | High | Worldwide |
|   | Not identified | adw3 | Low | Eastern Europe, Spain |
|   | D2 | ayw4 | Low | Eastern Europe, Spain, United States |
| E | — | ayw4 | High | Africa |
| F | F1, F2 | adw4q- | High | Latin America, Alaska, Pacific |
|   | F1, F2 | ayw4 | Low | Latin America |
| G | — | adw2 | Low | Europe, North America |
| H | — | ayw4 | Low | Central America |

*J. Med. Virol*, DOI 10.1002jmv

The HBV genome is a circular DNA molecule that is primarily double stranded but which has a single stranded region arising from one strand being longer than the other The double stranded region arises from the hybridization of one strand of a shorter strand of about 3020 nucleotides to a longer strand of about 3320 nucleotides. The single stranded region on non-hybridized nucleotides of the longer strand is associated with the HBV DNA polymerase. The HBV genomic DNA and HBV DNA polymerase are both contained within a nucleocapsid formed by multiple HBV core protein (HBcAg) molecules. The HBV core protein is enveloped by HBV surface protein (HBsAgs) and lipid molecules.

The HBV genome contains four open reading frames (ORFs): 1) an ORF that encodes the HBV DNA polymerase, 2) an ORF that has two start codons, wherein the sequence linked to the second start codon encodes the core protein and the sequence that includes the additional upstream start codon encodes a sequence referred to as pre-C; 3) an ORF that has three start codons, wherein one encodes the surface protein (gp27), one includes an upstream start codon which encodes a sequence referred to as pre-S2 (gp36) and another which includes a start codon further upstream which encodes a sequence referred to as pre-S1 (gp42); and 4) an ORF that encodes HBxAg, a protein whose function is less understood.

Prophylactic vaccines and therapies for HBV infection involve injection of subviral particles purified from plasma of chronic carriers, or subviral particles produced as recombinant proteins in stably transfected eukaryotic cell lines. The subviral particles are viral proteins and such vaccines are often referred to as subunit vaccines. The HBV proteins are administered to an individual and become targets for the individual's immune system. In uninfected individuals, an immune response against the subunit vaccine protects the uninfected individual from HBV infection. In infected individuals, the immune response induced by the vaccine can have therapeutic effects.

Chisari F. V., Am J Pathol., 2000. 156:1117-1132 and Pumpeus P. et al. Intervirology 2001. 44:98-114 disclose HBV genomic organization. Deny P. and F. Zoulim, Pathologic Biologic 2010, August, 58(4):245 53 discuss hepatitis B virus diagnosis and treatment. Michel M. L. and P. Tiollais, Pathologic Biologic 2010, August, 58(4):288 95 discuss hepatitis B vaccines and their protective efficacy and therapeutic potential. PCT publication WO2004026899 discloses the use immunogen containing polypeptide sequence with HBV amino acid sequences. PCT published application WO2008093976 discloses HBV coding sequences, proteins and vaccines including a vaccine comprising a recombinant full length HBV surface antigen and HBV core antigen. The entire HBV surface antigen consists of three types of surface protein (L protein, M protein and S protein). PCT published application WO2009130588 discloses HBV coding sequences, proteins and vaccines including a nucleic acid encoding a hepatitis B virus core antigen that is codon optimized for expression in humans. PCT publication WO2010127115 discloses delivery of HBV sequences using recombinant vectors.

The available HBV vaccines have exhibited some efficacy, but are costly to produce. In addition, plasma-derived subunit vaccines also have concerns about safety. Several vaccine approaches have been explored including those based on recombinant live vectors, synthetic peptides, and DNA vaccines that comprise codon optimized coding sequences of HBV proteins. These other approaches have thus far had varying limited efficacy. Additionally, due to genomic differences, some HBV vaccines have exhibited positive efficacy in some geographic areas and limited efficacy in other areas.

The direct administration of nucleic acid sequences to vaccinate against animal and human diseases has been studied and much effort has focused on effective and efficient means of nucleic acid delivery in order to yield necessary expression of the desired antigens, resulting immunogenic response and ultimately the success of this technique.

DNA vaccines allow for endogenous antigen synthesis, which induces CD8+ histocompatible complex, class I-restricted cytotoxic T lymphocytes that are rarely obtained with subunit vaccines. In addition, the antigen synthesis that occurs over a sustained period can help overcome low responsiveness and eliminate or reduce the requirement for booster injections. Further, DNA vaccines appear to be very stable and simple to produce. Moreover, broader cellular immune responses can be induced by combining strategies like codon optimization, RNA optimization and adding immunoglobulin leader sequences.

DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40].

Recent technological advances in the engineering of DNA vaccine immunogen have improved expression and immunogenicity of DNA vaccines, such has codon optimization, RNA optimization and the addition of immunoglobulin leader sequences [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. The in vivo electroporation technique has been used in human clinical trials to deliver anti-cancer drugs, such as bleomycin, and in many preclinical studies on a large number of animal species. In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

There remains a need for nucleic acid constructs that encode HBV antigens and for compositions useful to induce immune responses against HBV. There remains a need for effective vaccines against HBV that are economical and effective. There remains a need for effective vaccines that increase neutralizing antibody levels and elicit a T-cell component. There remains a need for effective vaccines against HBV, including those that are effective against HBV strains having a broad range of genotypes, and preferably, a universal vaccine that would be globally effective.

SUMMARY OF THE INVENTION

An aspect of the present invention includes vaccines useful for inducing an immune response against HBV. The development of an HBV immune therapeutic vaccine with broad effectiveness against a multitude of genotypes can be provided using a therapeutic DNA vaccine for HBV infection based on targeting the universally conserved HBV-core specific antigens. The utilization of consensus HBV immunogens induces broader cellular immune responses and can be useful to minimize the degree of sequence dissimilarity among different virus strains.

Provided herein are proteins selected from the group consisting of: proteins comprising SEQ ID NO:2, proteins that are 95% homologous to SEQ ID NO:2; fragments of SEQ ID NO:2; proteins that are 95% homologous to a fragment of SEQ ID NO:2; SEQ ID NO:4, proteins that are 95% homologous to SEQ ID NO:4; fragments of SEQ ID NO:4; proteins that are 95% homologous to a fragment of SEQ ID NO:4 SEQ ID NO:6, proteins that are 95% homologous to SEQ ID NO:6; fragments of SEQ ID NO:6; and proteins that are 95% homologous to a fragment of SEQ ID NO:6.

Nucleic acid molecules comprising sequences that encode one or more protein molecules set forth above are also provided. In some embodiments, the nucleic acid molecule comprises a sequence selected from the group consisting of: SEQ ID NO:1; a nucleic acid sequence that is 95% homologous to SEQ ID NO:1; a fragment of SEQ ID NO:1; a nucleic acid sequence that is 95% homologous to a fragment of SEQ ID NO:1; SEQ ID NO:3; a nucleic acid sequence that is 95% homologous to SEQ ID NO:3; a fragment of SEQ ID NO:3; a nucleic acid sequence that is 95% homologous to a fragment of SEQ ID N0:3; SEQ ID NO:5; a nucleic acid sequence that is 95% homologous to SEQ ID NO:5; a fragment of SEQ ID NO:5; and a nucleic acid sequence that is 95% homologous to a fragment of SEQ ID NO:5.

Some aspects of the invention provide methods of inducing an immune response against core antigen from one or more HBV genotypes comprising the step of: administering to an individual such nucleic acid molecules and/or compositions.

Additional aspects of the invention provide methods of protecting an individual against HBV infection. The methods comprise the step of: administering to said individual a prophylactically effective amount of a nucleic acid molecule comprising such nucleic acid sequence or compositions; wherein the nucleic acid sequence is expressed in cells of said individual and a protective immune response is induced against a protein encoded by said nucleic acid sequence.

In some aspects of the invention, methods are provided for treating an individual who has been infected by HBV. The methods comprise the step of: administering to said individual a therapeutically effective amount of such nucleic acid molecules and/or composition.

Aspects of the invention additionally related to vaccines comprising proteins or nucleic acids that encode proteins selected from the group consisting of: proteins comprising SEQ ID NO:2, proteins that are 95% homologous to SEQ ID NO:2; fragments of SEQ ID NO:2; proteins that are 95% homologous to a fragment of SEQ ID NO:2; SEQ ID NO:4, proteins that are 95% homologous to SEQ ID NO:4; fragments of SEQ ID NO:4; proteins that are 95% homologous to a fragment of SEQ ID NO:4 SEQ ID NO:6, proteins that are 95% homologous to SEQ ID NO:6; fragments of SEQ ID NO:6; and proteins that are 95% homologous to a fragment of SEQ ID NO:6. The vaccine may further comprise an adjuvant protein or a nucleic acid sequence that encodes an adjuvant protein. In some embodiments, the adjuvant is IL-12, IL-15, IL-28, or RANTES.

Vaccines that comprise nucleic acid molecules may comprise nucleic acid molecules that comprise nucleic acid sequences selected from the group consisting of: SEQ ID NO:1; a nucleic acid sequence that is 95% homologous to SEQ ID NO:1; a fragment of SEQ ID NO:1; a nucleic acid sequence that is 95% homologous to a fragment of SEQ ID NO:1; SEQ ID NO:3; a nucleic acid sequence that is 95% homologous to SEQ ID NO:3; a fragment of SEQ ID NO:3; a nucleic acid sequence that is 95% homologous to a fragment of SEQ ID NO:3; SEQ ID NO:5; a nucleic acid sequence that is 95% homologous to SEQ ID NO:5; a fragment of SEQ ID NO:5; and a nucleic acid sequence that is 95% homologous to a fragment of SEQ ID NO:5. The vaccine may further comprise a nucleic acid sequence that encodes an adjuvant protein. In some embodiments, the adjuvant is IL-12, IL-15, IL-28, or RANTES.

BRIEF DESCRIPTION OF THE FIGURES

FIG. 3A shows results from in vitro translation protocol.

FIGS. 3A and 3B show the enhanced magnitude of IFN-γ secretion in CD8+ and CD4+ T Cells from the spleens of C57BL/6 mice vaccinated with pM-Core.

DETAILED DESCRIPTION

Figure 1:
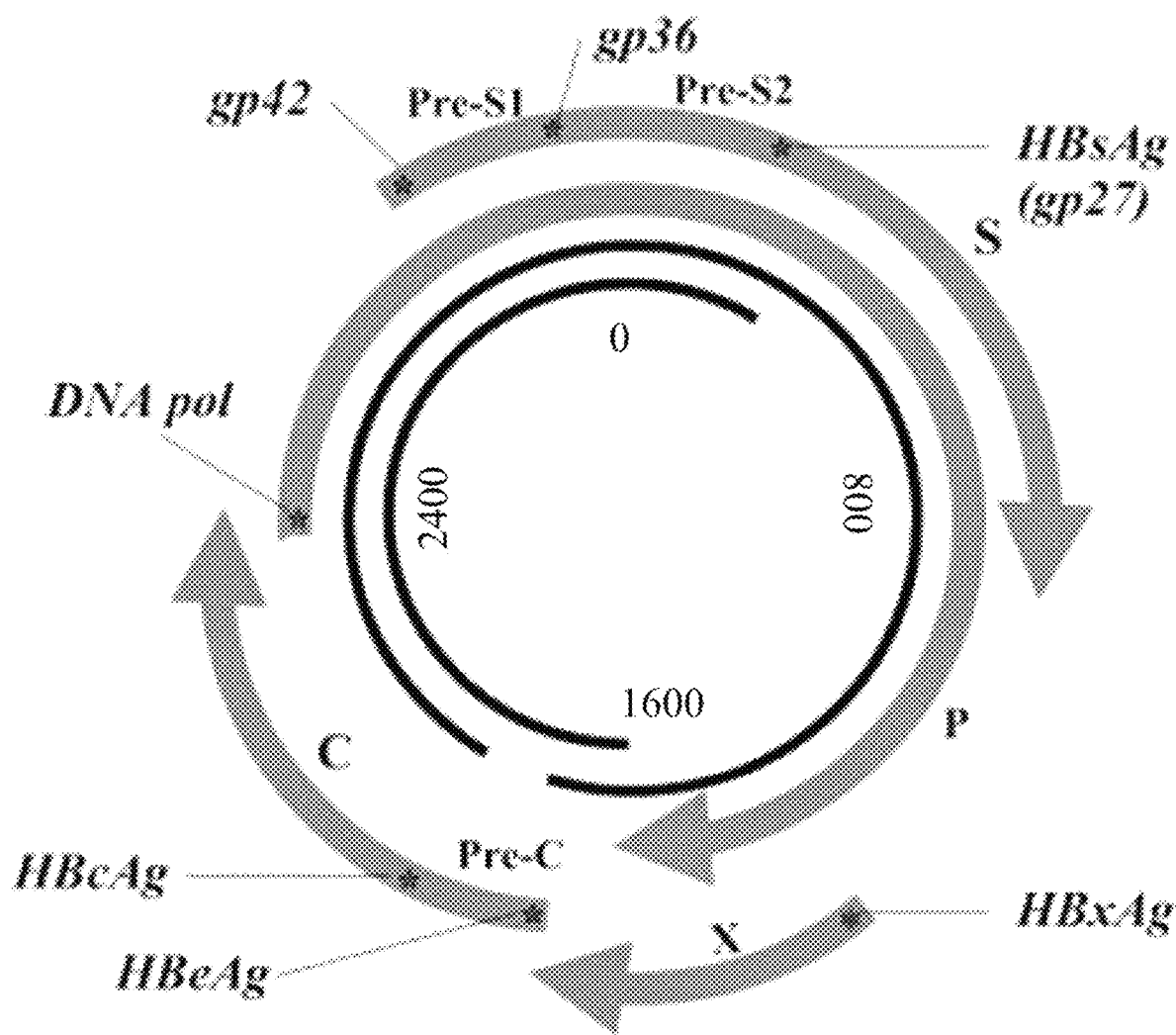
FIG. 1 is a map showing the organization of the HBV genome which consists of four overlapping ORFs.

1. Definitions.

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein means any molecule added to the DNA plasmid vaccines described herein to enhance the immunogenicity of the antigens encoded by the DNA plasmids and the encoding nucleic acid sequences described hereinafter.

b. Antibody

"Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

d. Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein means a polypeptide sequence based on analysis of an alignment of multiple subtypes of a particular HBV antigen. Nucleic acid sequences that encode a consensus polypeptide sequence can be prepared. Vaccines comprising proteins that comprise consensus sequences and/or nucleic acid molecules that encode such proteins can be used to induce broad immunity against multiple subtypes or serotypes of a particular HBV antigen.

f. Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

g. Fragment

"Fragment" as used herein with respect to nucleic acid sequences means a nucleic acid sequence or a portion thereof, that encodes a polypeptide capable of eliciting an immune response in a mammal that cross reacts with a full length wild type strain HBV antigen. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length wild type strain HBV antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus protein.

h. Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

i. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

j. Immune Response

"Immune response" as used herein means the activation of a host's immune system, e.g., that of a mammal, in response to the introduction of antigen such as an HBV consensus antigen. The immune response can be in the form of a cellular or humoral response, or both.

k. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

l. Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

m. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

n. Signal Peptide

"Signal peptide" and "leader sequence" are used interchangeably herein and refer to an amino acid sequence that can be linked at the amino terminus of an HBV protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein. As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences. Thus for example, SEQ ID NO:4 is SEQ ID NO:2 with the signal peptide/leader sequence linked at the N terminal of SEQ ID NO:2, i.e. SEQ ID NO:4 is a protein comprising a signal peptide linked to the N terminus of SEQ ID NO:2. The first residue in SEQ ID NO:2, "Xaa", is typically methionine when no signal peptide is present. However, proteins that comprise signal peptides linked to SEQ ID NO:2, such as SEQ ID NO:4, replace the residue 1 methionine at Xaa with the residue that links the signal peptide to the protein. Accordingly, the N terminal residue of SEQ ID NO:2 can be anything but if it is encoded by an initiation sequence it is methionine. The linkage of the signal peptide/leader sequence at the N terminal of SEQ ID NO:2 typically eliminates the N terminal methionine. As used herein, it is intended that SEQ ID NO:4 comprises SEQ ID NO:2 with a signal peptide/leader sequence linked at the N terminal of SEQ ID NO:2 notwithstanding the elimination of the N terminus Xaa residue of SEQ ID N0:2. Similarly, the coding sequences for SEQ ID NO:4 comprise coding sequences for SEQ ID NO:2 with coding sequences for a signal peptide/leader sequence linked to the 5' end of the coding sequences encoding SEQ ID NO:2. The initiation codon can be the "nnn" in the coding sequences for SEQ ID NO:2 but it is eliminated when the coding sequences for a signal peptide/leader sequence linked to the 5' end of the coding sequences encoding SEQ ID NO:2. As used herein, it is intended that coding sequences for SEQ ID NO:4 comprises coding sequences for SEQ ID NO:2 with coding sequences for a signal peptide/leader sequence linked at the 5' end of the coding sequence of SEQ ID NO:2 where nnn occurs. Thus, for example, it is intended that SEQ ID NO:3 comprises SEQ ID NO:1 with coding sequences for a signal peptide/leader sequence linked at the 5' end of SEQ ID NO:1, in place of the nnn. In some embodiments, the nnn is an initiation codon at the 5' end of SEQ ID NO:1.

o. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

p. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

q. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

r. Subtype or Serotype

"Subtype" or "serotype": as used herein, interchangeably, and in reference to HBV, means genetic variants of an HBV such that one subtype is recognized by an immune system apart from a different subtype.

s. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

t. Vector

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

2. HBV Core Antigen

The HBV core protein represents an important target for immune mediated viral clearance by inducing 1) cytotoxic T lymphocyte (CTL) responses, 2) T helper cell responses, and/or 3) B cell responses, or preferably all of the aforementioned, for cross presentation.

Table 2 shows the similarities across genotypes for core antigen from HBV-A, HBV-B, HBV-C, HBV-D and HBV-E genotypes with the consensus HBV core proteins, referred to in the chart as "HBV-M-core". For some embodiments, the HBV M Core construct was designed to have increased homologies for broad HBV core targets. Similarities Across Genotypes for Core Antigen with designed M-Core construct—increased homologies for broad HBV core targets. All genotypes should be represented in a universal immune therapeutic vaccine for HBV.

TABLE 2

| Divergence | | Percent Identity | | | | | |
|---|---|---|---|---|---|---|---|
| | 1 | | 96.2 | 96.2 | 97.8 | 95.6 | 98.4 | 1 - HBV-A-ConCore |
| | 2 | 3.9 | | 100 | 95.6 | 93.4 | 96.7 | 2 - HBV-B-ConCore |
| | 3 | 3.9 | 0 | | 95.6 | 93.4 | 96.7 | 3 - HBV-C-ConCore |
| | 4 | 2.2 | 4.5 | 4.5 | | 97.8 | 97.8 | 4 - HBV-D-ConCore |
| | 5 | 4.5 | 6.9 | 6.9 | 2.2 | | 95.6 | 5 - HBV-E-ConCore |
| | 6 | 1.7 | 3.4 | 3.4 | 2.2 | 4.5 | | 6 - HBV-M-Core |
| | | 1 | 2 | 3 | 4 | 5 | 6 | |

Provided herein are antigens capable of eliciting an immune response in a mammal against one or more HBV serotypes. The antigen can comprise core protein epitopes that make them particularly effective as immunogens against which anti-HBV immune responses can be induced. The HBV antigen can comprise the full length translation product, a variant thereof, a fragment thereof or a combination thereof.

A consensus HBV core protein (SEQ ID NO:2) is provided. Amino acid sequence was generated which comprised the IgE leader at the N terminus of the HBV core protein consensus sequences. Thus, also provided are a protein with an IgE leader (SEQ ID NO:7) linked to consensus HBV core protein (SEQ ID NO:2) to provide an IgE leader-consensus HBV core protein (SEQ ID NO:4). Some embodiments provided also comprise an HA tag (SEQ ID NO:8) linked at the C terminus of the HBV core protein consensus sequence. Accordingly, an HBV core protein consensus protein (SEQ ID NO:6) is provided which comprises an IgE leader (SEQ ID NO:7) linked to the HBV core protein consensus sequence (SEQ ID NO:2) and an HA Tag (SEQ ID NO:8) linked to the C terminal of the HBV core protein consensus sequences.

Proteins can be homologous to SEQ ID NO:2, SEQ ID NO:4, and SEQ ID NO:6. Some embodiments relate to immunogenic proteins that have 95% homology to the consensus protein sequences herein. Some embodiments relate to immunogenic proteins that have 96% homology to the consensus protein sequences herein. Some embodiments relate to immunogenic proteins that have 97% homology to the consensus protein sequences herein. Some embodiments relate to immunogenic proteins that have 98% homology to the consensus protein sequences herein. Some embodiments relate to immunogenic proteins that have 99% homology to the consensus protein sequences herein.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:2, SEQ ID NO:4 and SEQ ID NO:6 can be provided. Immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of SEQ ID NO:2, SEQ ID NO:4 and SEQ ID NO:6. In some embodiments, fragments include an leader sequence, such as for example an immunoglobulin leader, such as the IgE leader. In some embodiments, fragments are free of a leader sequence. In some embodiments, fragments are free of a leader sequence the IgE leader.

Immunogenic fragments of proteins with amino acid sequences homologous immunogenic fragments of SEQ ID NO:2, SEQ ID NO:4 and SEQ ID NO:6 can be provided. Such immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of proteins that are 95% homologous to S SEQ ID NO:2, SEQ ID NO:4 and SEQ ID NO:6. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include an leader sequence, such as for example an immunoglobulin leader, such as the IgE leader. In some embodiments, fragments are free of a leader sequence. In some embodiments, fragments are free of a leader sequence the IgE leader.

3. Genetic Sequences, Constructs and Plasmids

Nucleic acid sequences encoding the SEQ ID NO:2, SEQ ID NO:4 and SEQ ID NO:6 as well as homologous protein, immunogenic fragment and immunogenic fragments of homologous proteins can be generated routinely. Thus, nucleic acid molecules that encode immunogenic proteins that have up to 95% homology to a consensus sequence, up to 96% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of protein homologous to the proteins set forth herein are also provided.

Nucleic acid molecules encoding the consensus amino acid sequences were generated. Vaccines can comprise one or more nucleic acid sequences that encode one or more of the consensus versions of the immunogenic proteins selected from this group of sequences generated to optimize stability and expression in humans. Nucleic acid sequence (SEQ ID NO:1) encoding the HBV core protein consensus protein (SEQ ID NO:2), nucleic acid sequence (SEQ ID NO:3) encoding the IgE leader-HBV core protein consensus protein(SEQ ID NO:4), and nucleic acid sequence (SEQ ID NO:5) encoding IgE leader-HBV core protein consensus protein—HA Tag (SEQ ID NO:6). Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:1, SEQ ID NO:3 and SEQ ID NO:5. Fragments can be at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of SEQ ID NO:1, SEQ ID NO:3 and SEQ ID NO:5. Fragments can be at least 95%, at least 96%, at least 97% at least 98% or at least 99% homologous to fragments of SEQ ID NO:1, SEQ ID NO:3 and SEQ ID NO:5. In some embodiments, fragments include sequences that encode an leader sequence, such as for example an immunoglobulin leader, such as the IgE leader. In some embodiments, fragments are free of coding sequences that encode a leader sequence. In some embodiments, fragments are free of coding sequences that encode a leader sequence the IgE leader.

Provided herein are genetic constructs that can comprise a nucleic acid sequence that encodes the HBV core antigen disclosed herein including consensus protein sequences, sequences homologous to consensus protein sequences, fragments of consensus protein sequences and sequences homologous to fragments of consensus protein sequences. The genetic construct can be present in the cell as a functioning extrachromosomal molecule. The genetic construct can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an antigen, which the transformed host cell is cultured and maintained under conditions wherein expression of the antigen takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding an antigen and can further comprise an initiation codon, which can be upstream of the antigen coding sequence, and a stop codon, which can be downstream of the antigen coding sequence. The initiation and termination codon can be in frame with the antigen coding sequence. The vector can also comprise a promoter that is operably linked to the antigen coding sequence. The promoter operably linked to the antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the HBV core protein coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus HBV core protein coding sequence. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G 241 in CMV promoter
C>T 1942 backbone, downstream of the bovine growth hormone polyadenylation signal (bGHpolyA)
A>-2876 backbone, downstream of the Kanamycin gene
C>T 3277 in pUC origin of replication (Ori) high copy number mutation (see Nucleic Acid Research 1985)
G>C 3753 in very end of pUC Ori upstream of RNASeH site
Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus HBV coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which maybe used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

4. Pharmaceutical Compositions

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanograms to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

Provided herein is a vaccine capable of generating in a mammal an immune response against one or more genotypes of HBV. The vaccine can comprise the genetic construct as discussed above.

While not being bound by scientific theory, the vaccine can be used to elicit an immune response (humoral, cellular, or both) broadly against one or more genotypes of HBV. Vaccines can comprise coding sequences for consensus HBV core protein sequence (SEQ ID NO:2); IgE leader linked to consensus HBV core protein sequence (SEQ ID NO:4); and IgE leader linked to consensus HBV core protein linked to HA Tag sequence (SEQ ID NO:6). Vaccines can comprise specific coding sequences for consensus HBV core protein sequence (SEQ ID NO:2) such as (SEQ ID NO:1); IgE leader linked to consensus HBV core protein sequence (SEQ ID NO:4) such as (SEQ ID NO:3) and IgE leader linked to consensus HBV core protein linked to HA Tag sequence (SEQ ID NO:6) such as (SEQ ID NO:5).

Some alternative embodiments include those which comprise nucleic acid sequences encoding immunogenic fragments of consensus HBV core protein, one or more proteins homologous to consensus HBV core protein, and immunogenic fragments of one or more proteins homologous to consensus HBV core protein.

Some embodiments provide methods of generating immune responses against HBV core proteins comprise administering to an individual one or more compositions described herein. Some embodiments provide methods of prophylactically vaccinating an individual against HBV infection comprise administering one or more compositions described herein. Some embodiments provide methods of therapeutically vaccinating an individual has been infected with HBV comprise administering one or more compositions described herein. Diagnosis of HBV infection prior to administration can be done routinely.

The vaccine can be a DNA vaccine. The DNA vaccine can comprise a plurality of the same or different plasmids comprising nucleic acid sequences encoding consensus HBV core protein.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the HBV core protein. The RNA vaccine can be introduced into the cell.

The vaccine can be a recombinant vaccine comprising the genetic construct or antigen described above. The vaccine can also comprise one or more consensus HBV core protein in the form of one or more protein subunits, one or more killed viral particles comprising one or more consensus HBV core protein, or one or more attenuated viral particles comprising one or more consensus HBV core protein. The attenuated vaccine can be attenuated live vaccines, killed vaccines and vaccines that use recombinant vectors to deliver foreign genes that encode one or more consensus HBV core protein, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can comprise vectors and/or proteins directed to multiple HBV genotypes from multiple particular regions in the world. The vaccine provided can be used to induce immune responses including therapeutic or prophylactic immune responses. Antibodies and/or killer T cells can be generated which are directed to the consensus HBV core protein, and also broadly across multiple genotypes of HBV viruses. Such antibodies and cells can be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

5. Methods of Delivery

Provided herein is a method for delivering the pharmaceutical formulations, preferably vaccines, for providing genetic constructs and proteins of the HBV core protein which comprise epitopes that make them particular effective immunogens against which an immune response to HBV viral infections can be induced. The method of delivering the vaccine, or vaccination, can be provided to induce a therapeutic and/or prophylactic immune response. The vaccination process can generate in the mammal an immune response against a plurality of HBV genotypes. The vaccine can be delivered to an individual to modulate the activity of the mammal's immune system and enhance the immune response. The delivery of the vaccine can be the transfection of the HA antigen as a nucleic acid molecule that is expressed in the cell and delivered to the surface of the cell upon which the immune system recognized and induces a cellular, humoral, or cellular and humoral response. The delivery of the vaccine can be use to induce or elicit and immune response in mammals against a plurality of HBV viruses by administering to the mammals the vaccine as discussed herein.

Upon delivery of the vaccine to the mammal, and thereupon the vector into the cells of the mammal, the transfected cells will express and secrete consensus HBV core protein. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with an HBV viral strain, the primed immune system will allow for rapid clearing of subsequent HBV viruses, whether through the humoral, cellular, or both. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. Combination Treatments

The pharmaceutical compositions, preferably vaccines described herein, can be administered combination with proteins or genes encoding adjuvants, which can include: α-interferon (IFN-α), β-interferon (IFN-β), γ-interferon, IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, or TAP2, or functional fragments thereof.

b. Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The HBV antigen can be delivered via DNA injection and along with in vivo electroporation.

c. Electroporation

Administration of the vaccine via electroporation of the plasmids of the vaccine can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

d. Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLE

The present invention is further illustrated in the following examples. It should be understood that these examples, while indicating preferred embodiments of the invention, is given by way of illustration only. From the above discussion and the examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

A consensus HBV core protein, also referred to as HBV modified or M-core construct, was designed from epitope sequences from HBV genotypes A, B, C, D and E. HBV core proteins sequences from these genotypes were selected for inclusion in a construction of a consensus core that would induce immunity against a broad range of genotypes, thus providing a universal vaccine for HBV. In some embodiments, modifications of the M-core construct included addition of a IgE leader sequence. In some embodiments, the M-core protein is encoded using codon optimization and RNA optimization for enhanced expression.

Figure 2A:
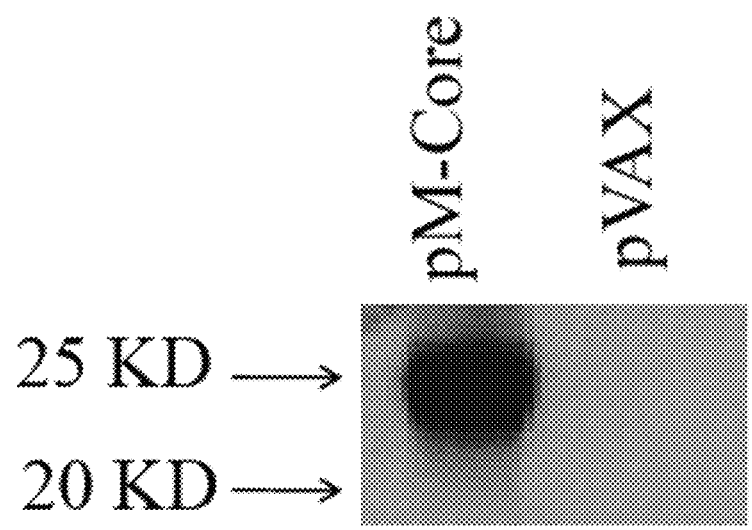
FIGS. 2A and 2B shows results from pM Core expression experiments.
Figure 2B:
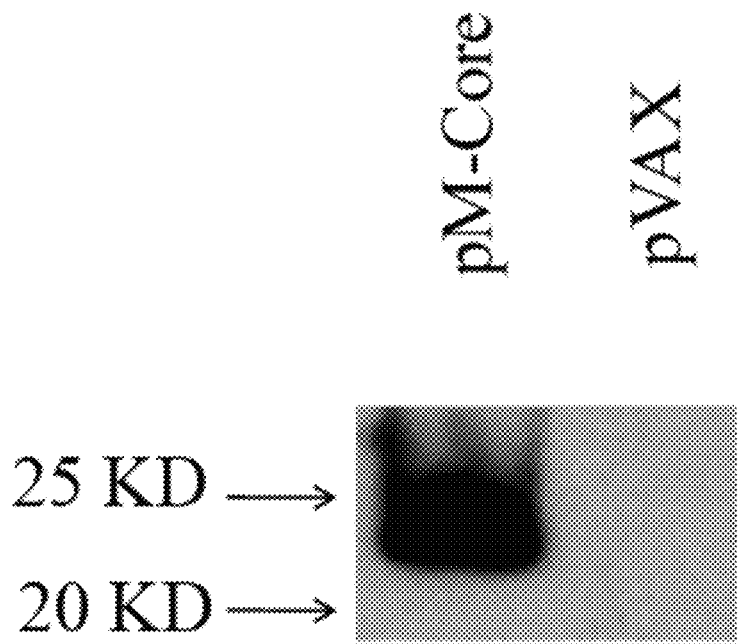

A nucleic acid sequence encoding M-core sequence with IgE leader and HA Tag (SEQ ID NO:5) was cloned into the expression vector pVAX to yield construct pM-core. In vitro expression tests were done using the pM construct and pVAX and was used as a control. The results showing positive expression are depicted in the gel images shown in FIGS. 2A and 2B.

C57BL/6 transgenic mice were separated into two groups of four mice each and using electroporation immunized three times with 20 μg DNA at biweekly intervals (group 1—pVAX vector control; group 2 pM-core). Mice were immunized on Day 0, Day 14, Day 28 and sacrificed on Day 35. Spleens, liver and sera were harvested from sacrificed the animals.

Figure 3B:
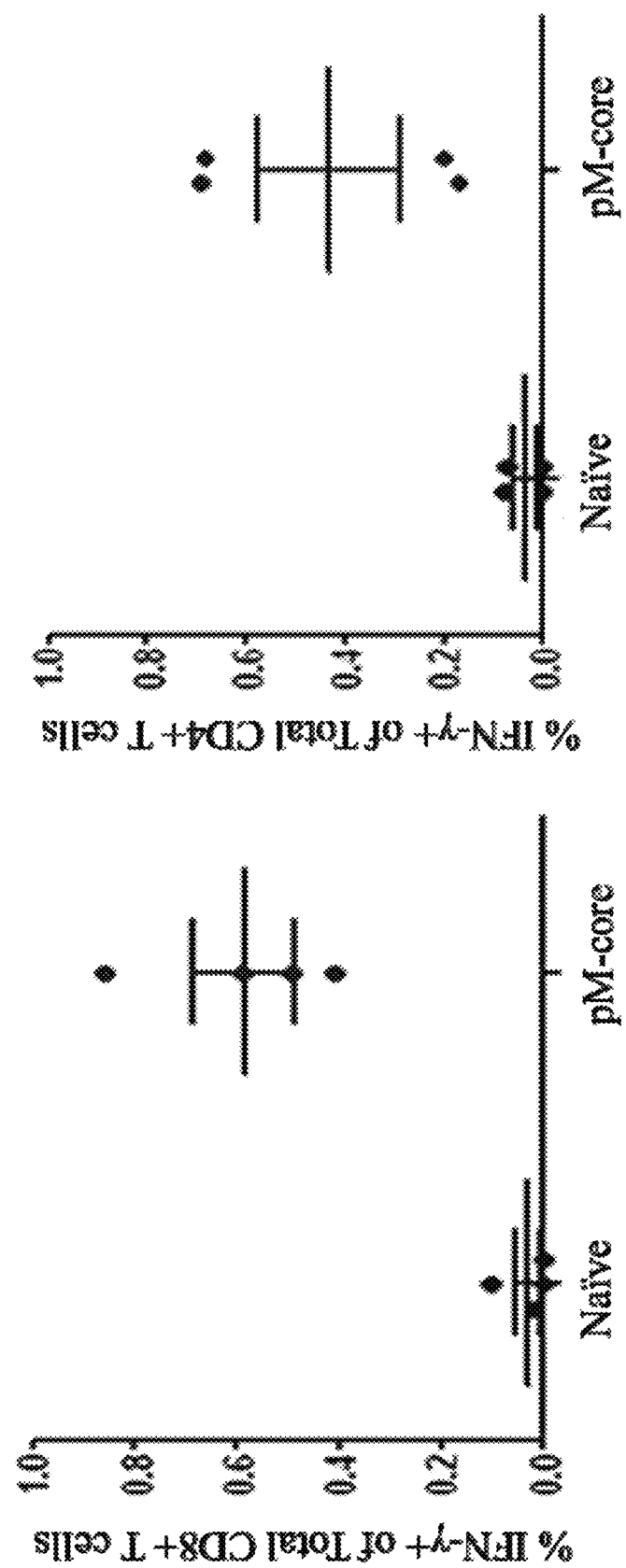
FIG. 3B shows results of a Western Blot.
Figure 4A:
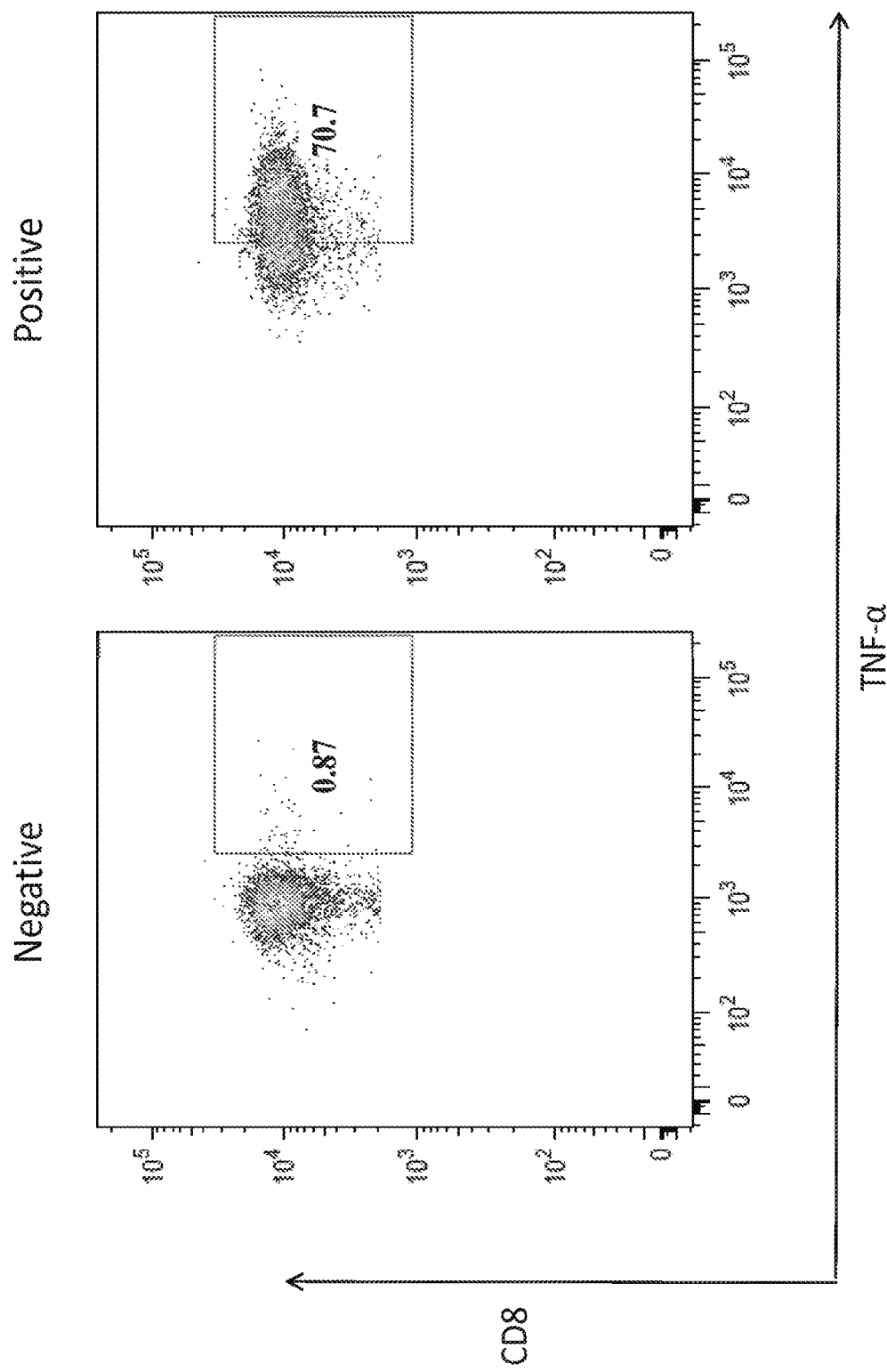
FIGS. 4A and 4B show the enhanced magnitude of TNF-α secretion in CD8+ and CD4+ T Cells from the spleens of C57BL/6 mice vaccinated with pM-Core.
Figure 4B:
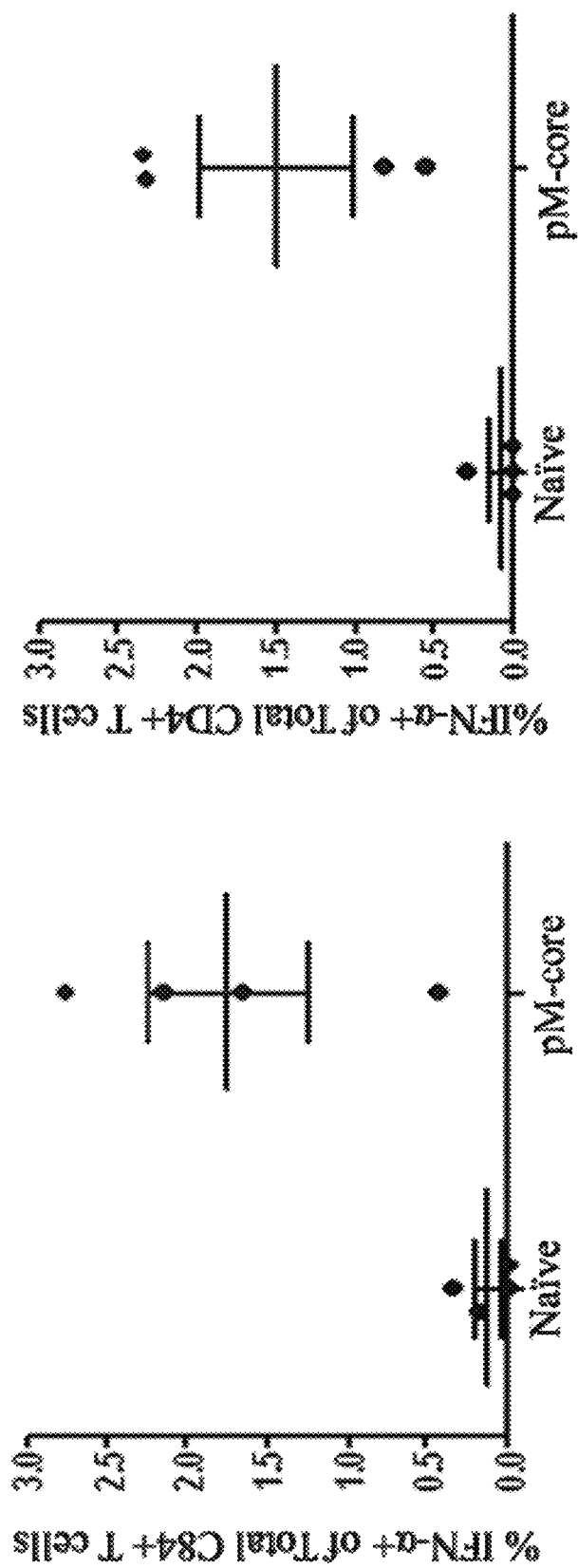
Figure 5A:
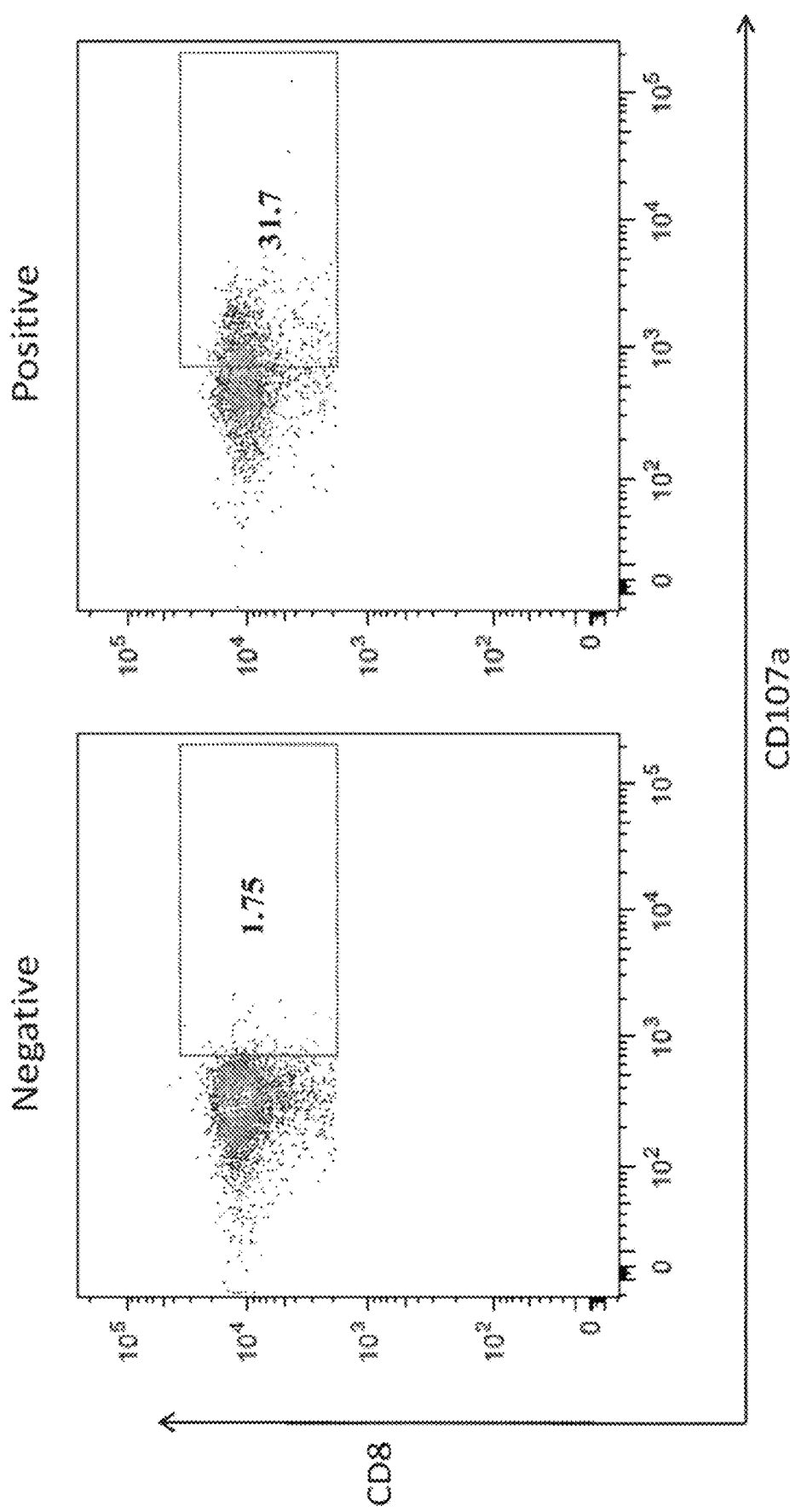
FIGS. 5A and 5B show the enhanced magnitude of CD 107a secretion in CD8+ and CD4+ T Cells from the spleens of C57BL/6 mice vaccinated with pM-Core.
Figure 5B:
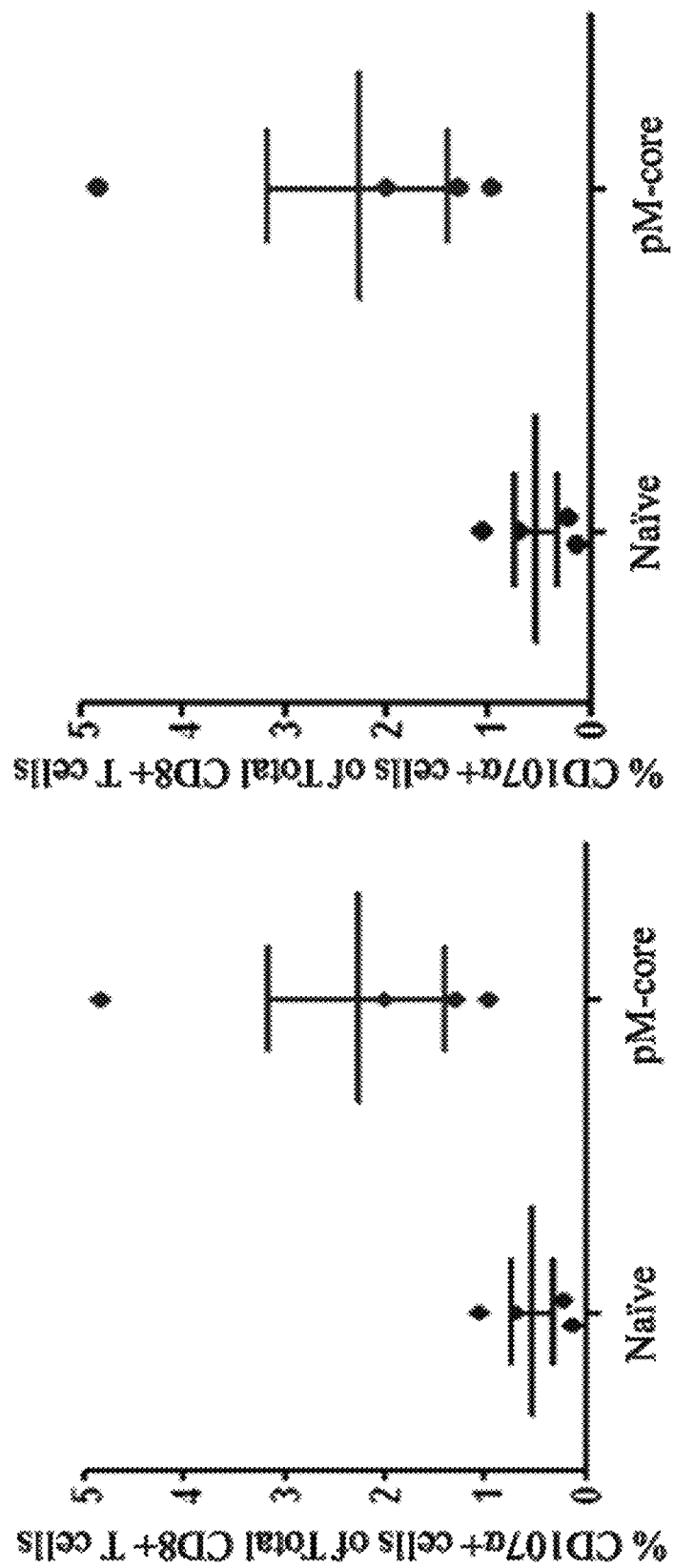

In vivo studies of C57BL/6 mice strains indicate enhancement in the magnitude of secretion of tumor necrosis factor (TNF-α), interferon gamma T-cell (IFN-γ) and the CD107a in the CD8 and CD4 T-cells taken from the spleen. FIGS. 3A and 3B show that vaccination of C57BL/6 mice with pM-Core enhanced the magnitude of IFN-γ secretion in CD8+ and CD4+ T Cells from the spleens. FIGS. 4A and 4B show that vaccination of C57BL/6 mice with pM-Core enhanced the magnitude of TNF-α secretion in CD8+ and CD4+ T Cells from the spleens. FIGS. 5A and 5B show that vaccination of C57BL/6 mice with pM-Core enhanced the magnitude of CD 107a secretion in CD8+ and CD4+ T Cells from the spleens.

Figure 6A:
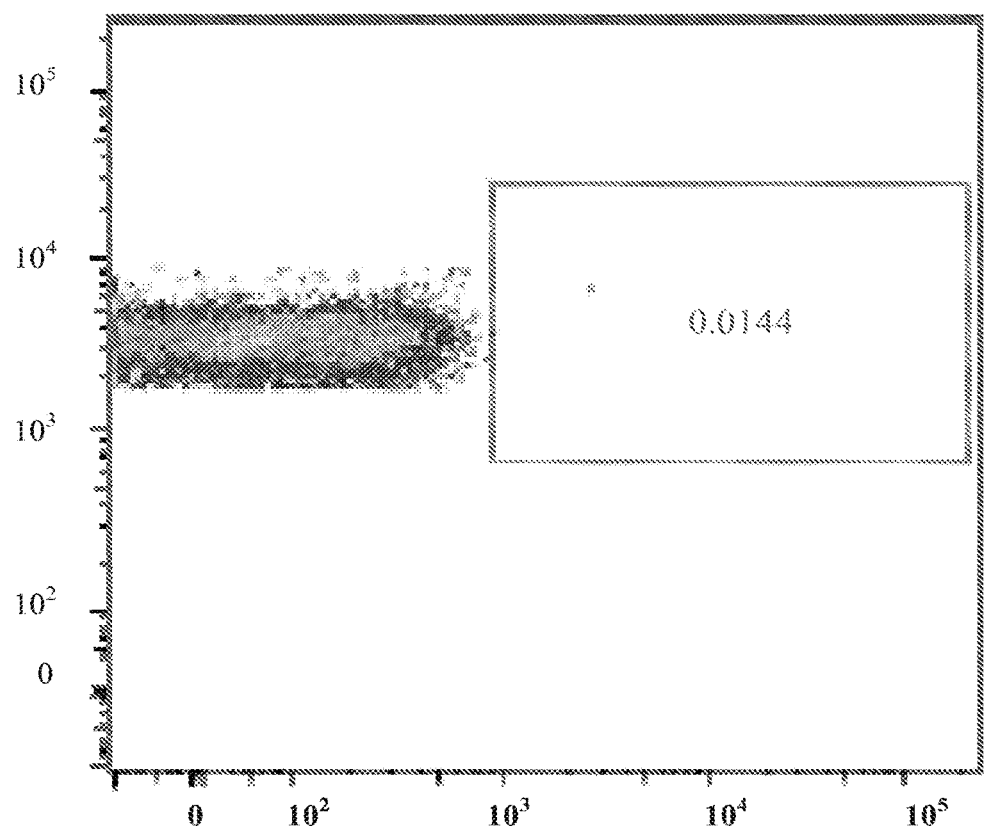
FIGS. 6A and 6B show interferon-gamma T cell response in liver from C57BL/6 mice vaccinated with pM-Core.
Figure 6B:
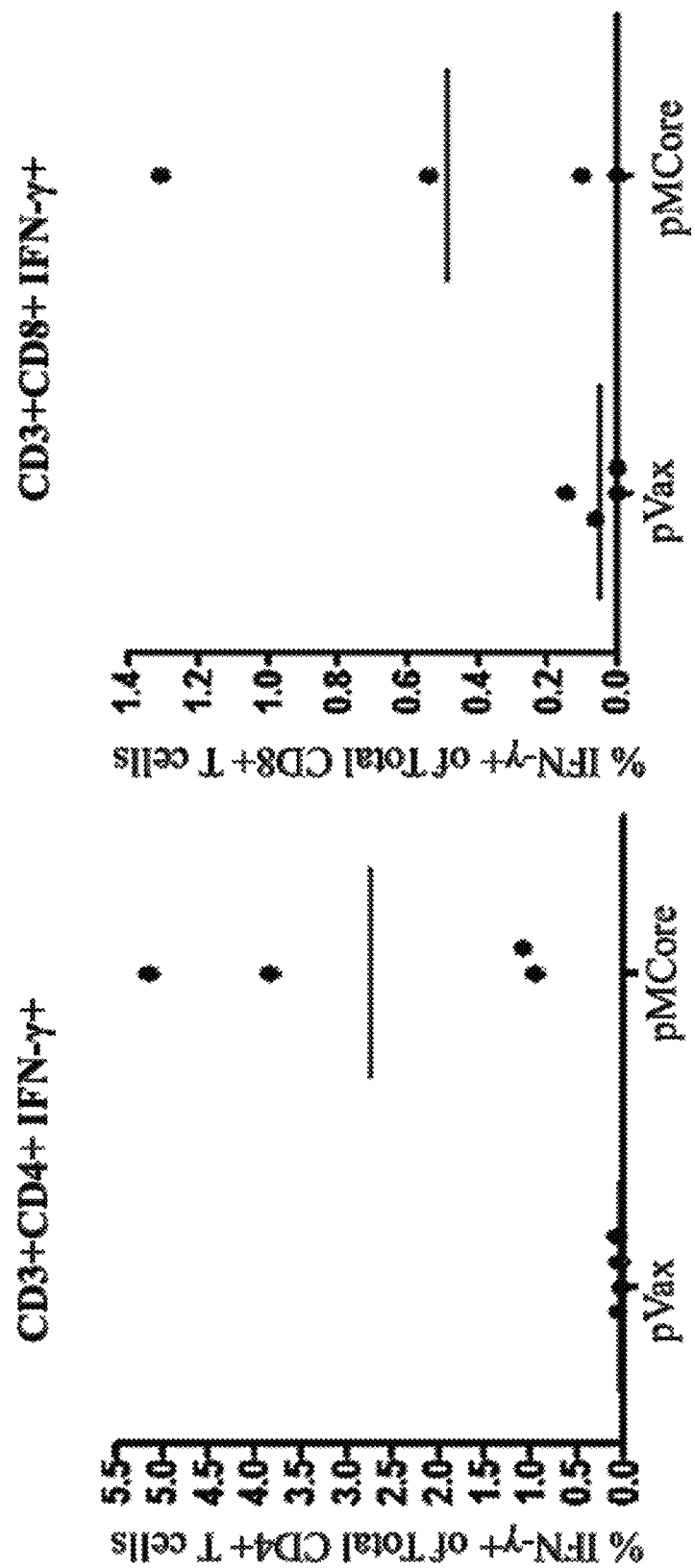
Figure 7A:
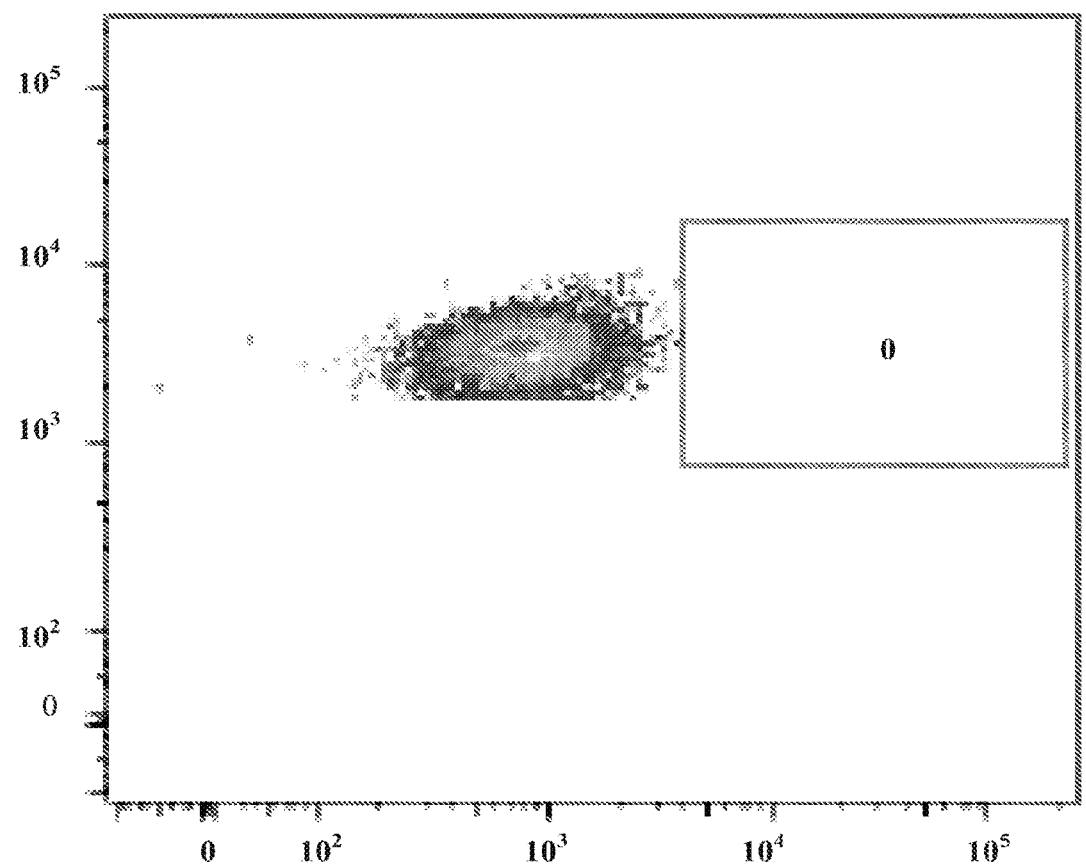
FIGS. 7A and 7B show Tumor Necrosis Factor-α T cell response in liver from C57BL/6 mice vaccinated with pM-Core.
Figure 7B:
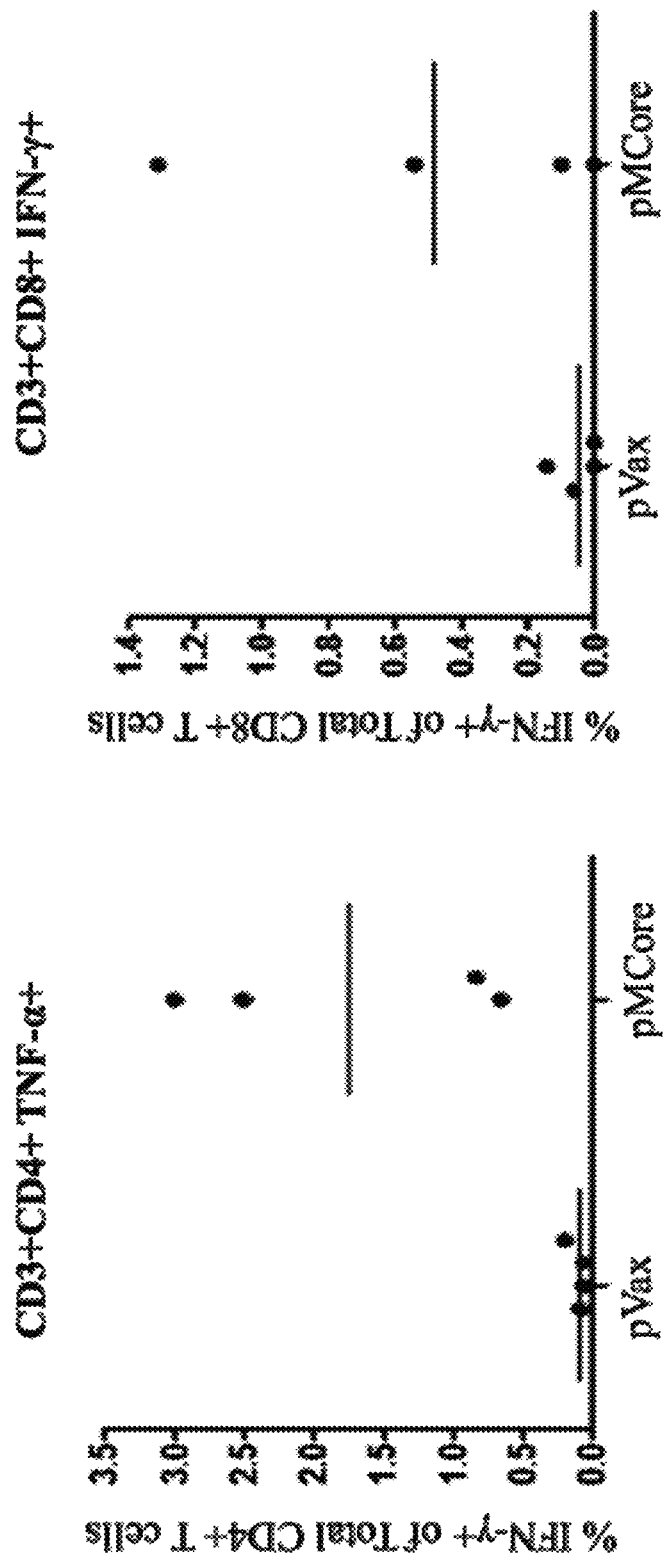

HBV specific T-cell migration to liver was also demonstrated in animals administered the pM-Core DNA vaccine. Targeting HBV core antigen-specific T cells with high frequency and effector function to the liver is an important goal for development of an HBV immune therapy. Following immunization, animals were sacrificed and their livers were removed and HBV specific effector T cell migration to the liver was determined. The results show that the pM-Core vaccine drives effector T cells to the liver in vivo. FIGS. 6A and 6B show interferon-γ T cell liver response, FIGS. 7A and 7B show Tumor Necrosis Factor-α liver immune response, and the elevated response that results from vaccination with pM-Core.

The M-core consensus immunogen encoded by the pM-core DNA construct drives strong balanced CD4+/CD8+ T cell immune responses. Induced T cells traffic to the liver at high frequency and exhibit the correct effector phenotype for immune clearance post HBV infection.

Figure 8:
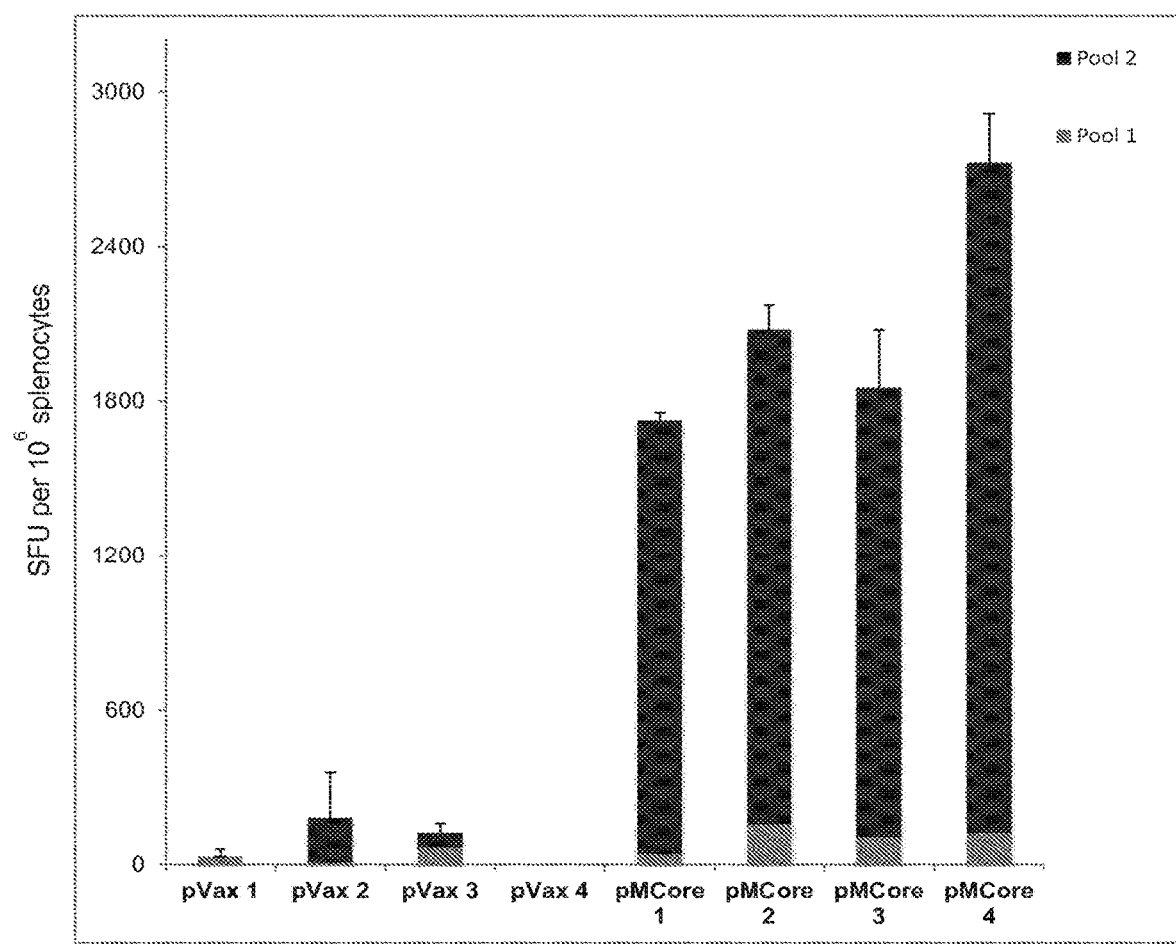
FIG. 8 shows data from ELISPOT assays.

FIG. 8 shows Cellular Immune responses Induced by pM-Core using an Enzyme-linked immunosorbent spot (ELISPOT) assay. Splenocytes were stimulated with two pools of 15-mer peptides spanning the entire length of pMCore and over lapping by 8 amino acids. 200,000 splenocytes in R10 media were plated in a 96 well IFN-γ capture antibody (R&D system) coated plate and stimulated overnight in the presence of a specific peptide pool at 37° C. in 5% $CO_2$. Cells were washed out and plates were incubated overnight with biotinylated anti-mouse IFN-γ detection antibody (R&D system). Streptavidin-alkaline phosphatase and 5-bromo-4-chloro-3'-indolylphosphate p-toluidine salt and nitro blue tetrazolium chloride were subsequently used to develop spots. Spots were counted using an automated ELISPOT reader (CTL Limited). As shown in FIG. 8, immunization with pMCore could induce strong cellular immune responses. The data showed that the dominant epitopes were biased towards peptide pool 2. The average HBcAg-specific IFN-γ T cell responses were about 2000 (±210) SFU per million splenocytes.

In vivo cytotoxicity assay studies were performed using carboxyfluorescein diacetate succinimidyl ester (CFSE) labeling combined with flow cytometry. Cell division at among cells of cell populations we assessed. Splenocytes were isolated from naïve mice and divided into two populations. One population, CFSE high labeled, was pulsed with relevant peptide (e.g. HBV core peptides). The other population, CFSE low labeled, was pulsed with irrelevant peptide (e.g. HCV NS3 peptides). The labeled, peptide treated cells were combined and used in adoptive transfer experiments in which flow analysis was performed. The combined populations of treated, labeled target cells were administered to two groups of mice, a control group and an immunized group. Splenocytes were isolated from each group of mice and samples were run on a flow cytometer. The amount of CFSE was measured. Typically, in such experiments, two peaks form, the first being the irrelevant peptide; the second being the immunizing peptide in the peak indicating greater CFSE.

Figure 9:
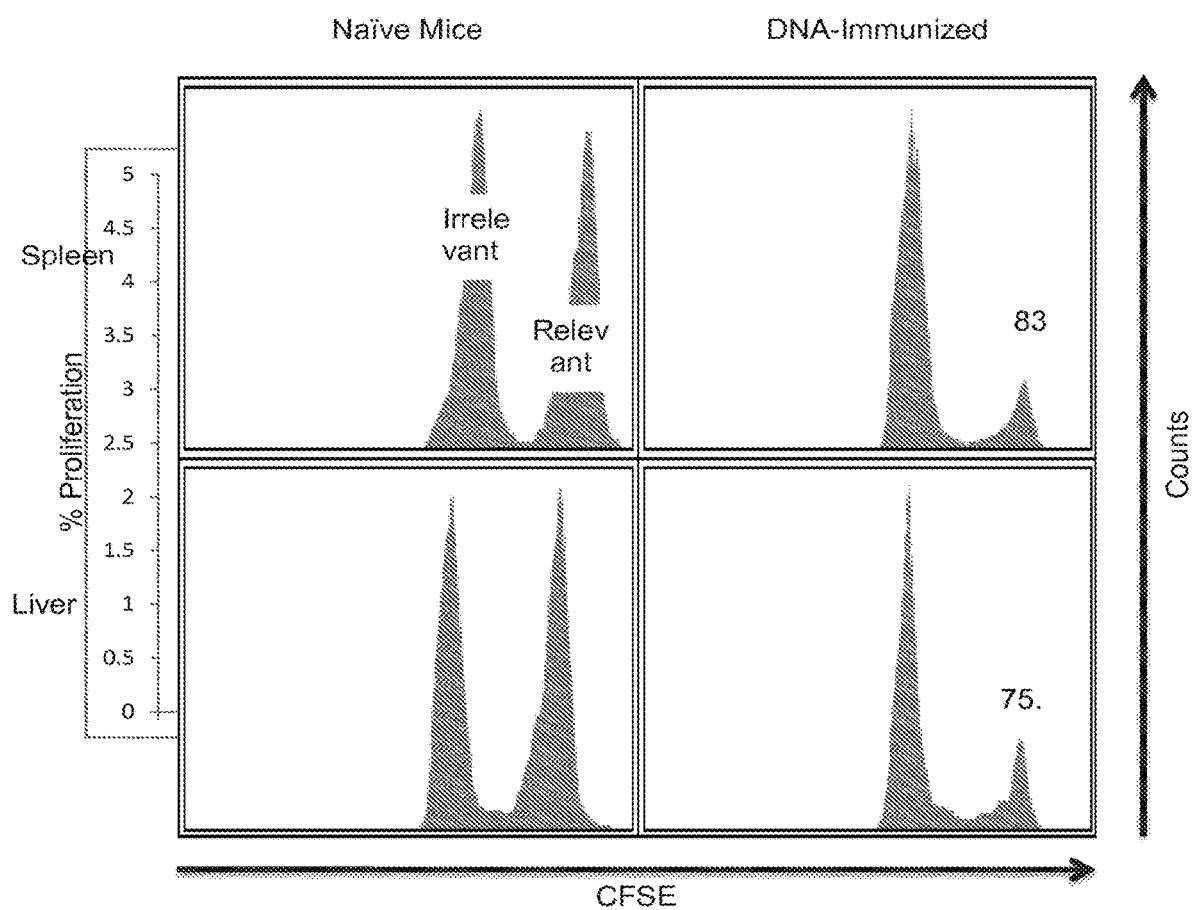
FIG. 9 shows data from experiments using CSFE labeled cells to compare elimination of peptide treated target cells in vivo by CD8 T cells in vaccinated and unvaccinated animals.

FIG. 9 shows that CD8 T cell induced by vaccination can specifically eliminate target cells in vivo. The results shows that samples of spleen and liver from naïve mice contained nearly equal amounts of cells which were in the irrelevant peptide and relevant peptide peaks while the results clearly show that among immunized groups, the peaks for cells derived from those pulsed with the relevant peptide were significantly less than irrelevant peptide. These data show that target cells treated with the HBV peptide were specifically eliminated in mice immunized with the HBV vaccine but not in the non-immunized mice. Any elimination of target cells treated with the irrelevant peptide, if it occurred at all, was the same in mice immunized with the HBV vaccine and the non-immunized mice and significantly less than elimination of target cells treated with the HBV peptide.

Figure 10:
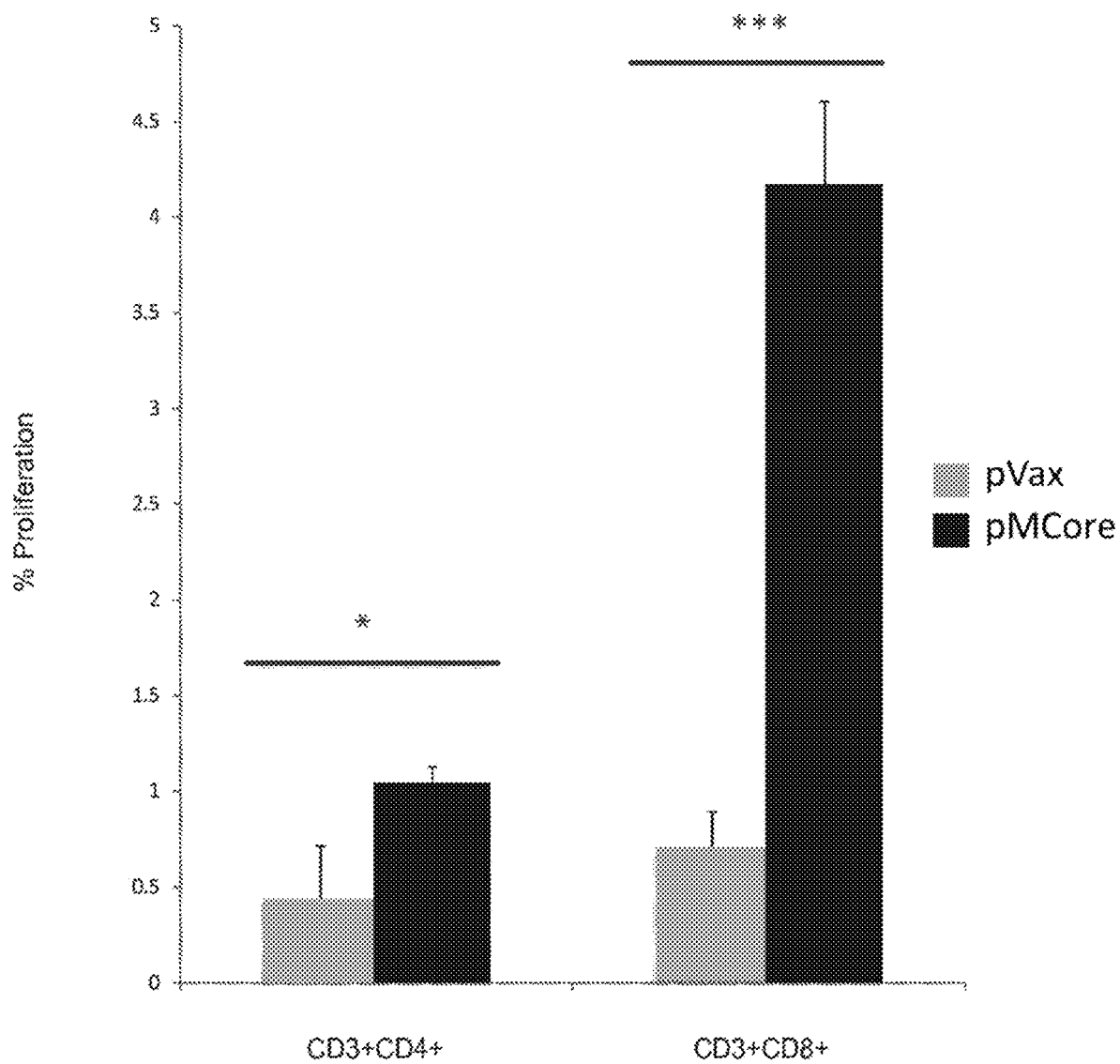
FIG. 10 shows a comparison of percent proliferation of CD3+CD4+ cells and CD3+CD8+ treated with pVax vector (control) or with plasmid pMCore which expresses HBV M-core.

FIG. 10 shows the data collected from the T cell Proliferation Assay using CFSE labeling. Percent proliferation of CD3+CD4+ cells and CD3+CD8+ treated with pVax vector (control) or with plasmid pMCore which expresses HBV M-core were compared. Briefly, the isolated splenocytes were stained with the carboxyfluorescein diacetate, succinimidyl ester (CFDA-SE) Cell Tracer Kit (Invitrogen) per the manufacturer's instructions. Stained cells were washed three times with saline and stimulated with the pMCore-specific overlapping peptides. The cells were incubated at 37° C. for 96 hours. After 48 hours, 50% of the culture media were removed and replaced with fresh R10. At day 4, cells were harvested and stained with CD3, CD4 and CD8-specific monoclonal antibodies (BD Pharmingen). Cells were fixed with PBS with 1% Paraformaldehyde (PFA) and acquired on a FACScalibur (Becton Dickinson). The data were analyses using FlowJo program. CFSE low and CFSE medium population was considered as proliferated cells. As shown in FIG. 10, the CD3+CD8+ T cells isolated from the spleen proliferated more compared to the CD3+CD4+ T cells.

Figure 11A:
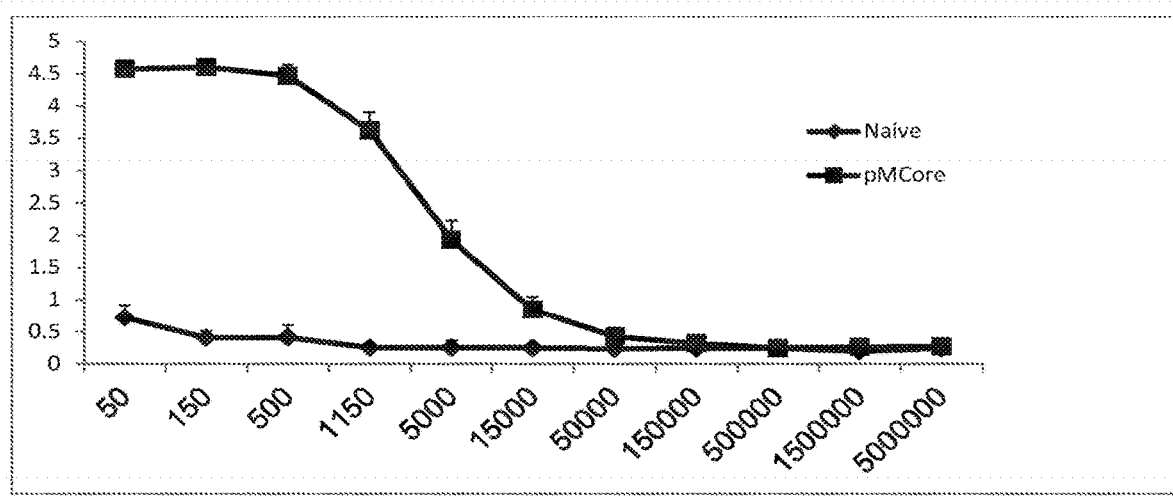
FIGS. 11A and 11B shows a comparison of anti-HBV core antibody in serial dilution of sera from animals treated with pVax vector (control) or with plasmid pMCore which expresses HBV M-core.
Figure 11B:
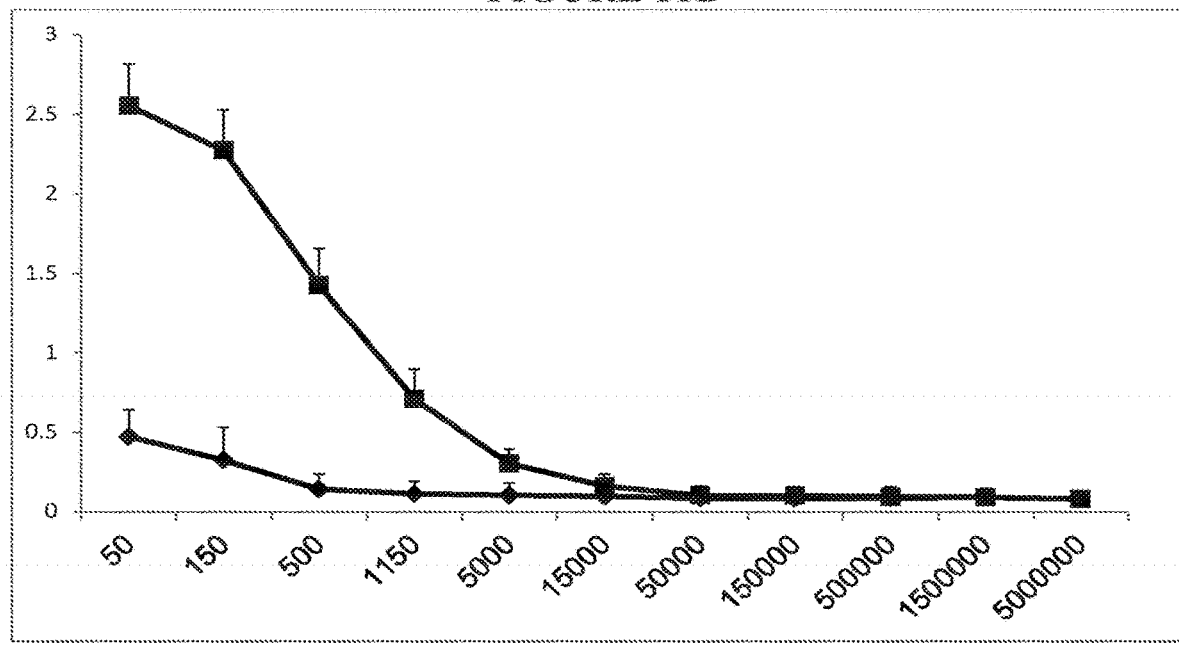

FIGS. 11A and 11B are ELISA data showing a comparison of anti-HBV core antibody in serial dilution of sera from animals treated with pVax vector (control) or with plasmid pMCore which expresses HBV M-core. Briefly, high-binding ELISA plates (Costar, Corning, N.Y.) were coated with 1 µg/ml HBcAg protein in PBS, at 4° C. for 24 h and then were washed with PBS-Tween and blocked with PBS containing 1% BSA for 2 h at room temperature. Serially diluted serum samples were added to the wells and incubated for 1 h at room temperature. After washing, bound serum antibody was revealed by HRP-labeled goat anti-mouse IgG (FIG. 11A) or IgA (FIG. 11B). The peroxidase-conjugated Abs were detected using tetramethylbenzidine (Sigma-Aldrich) as the substrate, and OD at 450 nm was measured with the Multiscan ELISA Plate Reader. The antigen-specific humoral response in sera collected from immunized mice were observed.

Figure 12:
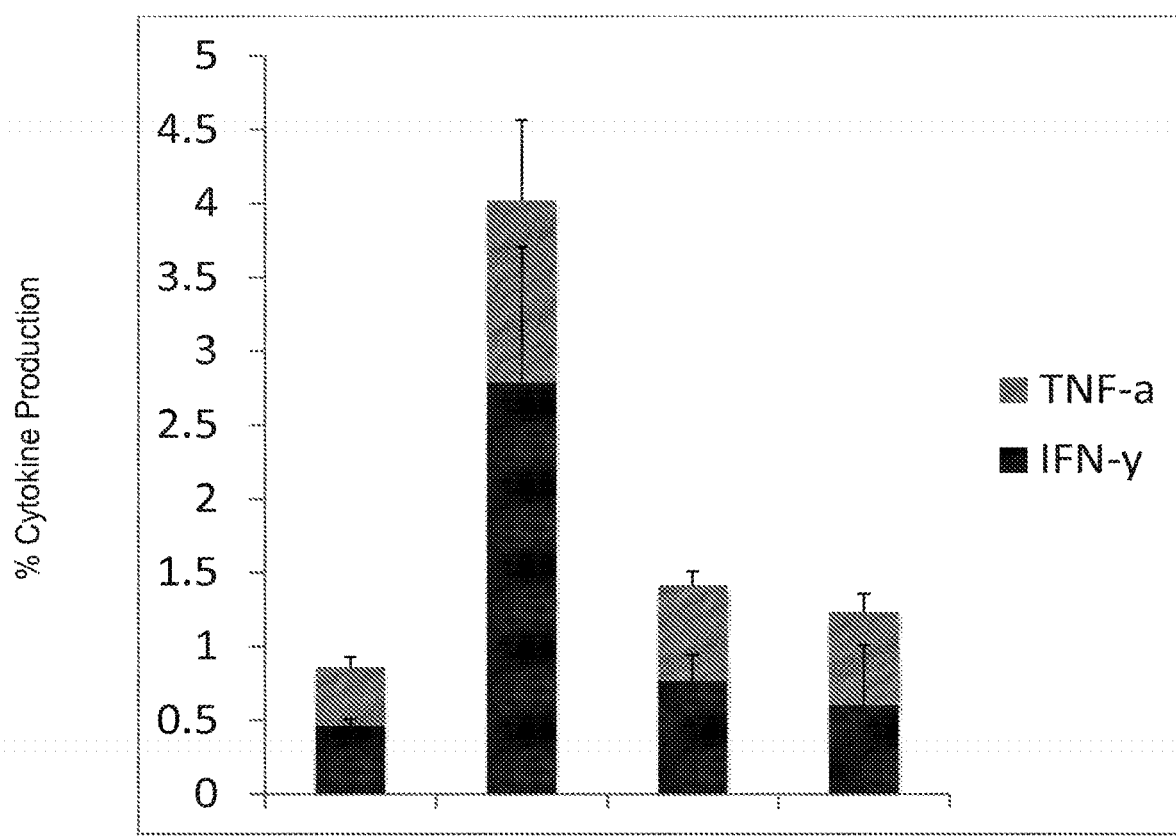
FIG. 12 shows percent TNF-a and IFN-g from CD4+ and CD8+ spleen and liver cells.

FIG. 12 shows percent TNF-α and IFN-γ from CD4+ and CD8+ spleen and liver cells.

Figure 13:
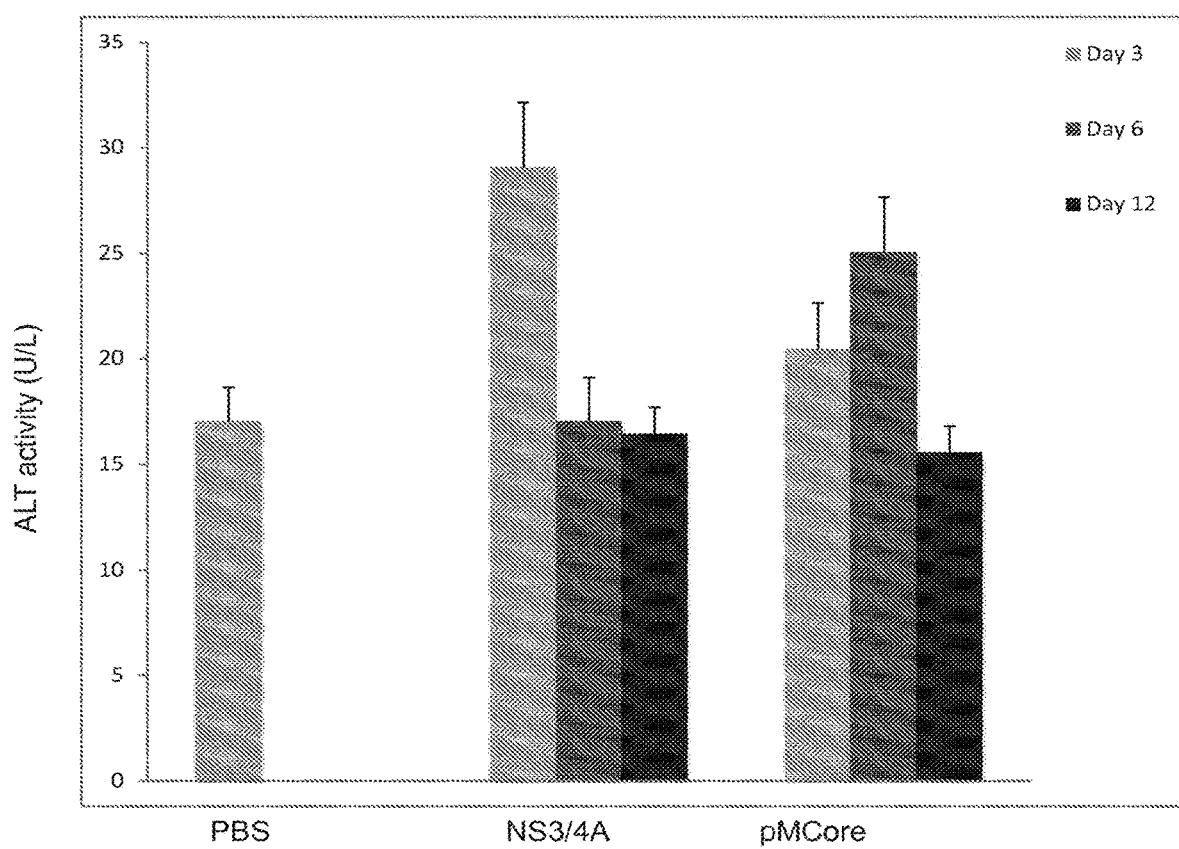
FIG. 13 show data from experiments to determine if clearance induced by the immunized mice did effects liver by measuring ALT levels in sera.

In the absence of a small animal model for HBV, HBcAg was used to transiently transfect mouse liver through hydrodynamic injection. Immunized mice liver were either transfected with pMCore or HCV NS3/4A. Immunohistochemistry staining three days post transfection showed clearance of HBcAg-transfected hepatocytes as compare to the NS3/4A-transfected ones. ALT levels in sera were measured to ensure that the clearance induced by the immunized mice did not cause any liver damage. Results in FIG. 13 show clearance induced by the immunized mice did not cause any liver damage

The invention claimed is:

1. An immunogenic composition comprising a nucleic acid molecule encoding an immunogenic fragment of a consensus hepatitis B virus (HBV) core protein that comprises at least 50% of the full length of SEQ ID NO:2, wherein the immunogenic fragment comprises serine residues at amino acids 74 and 87 of SEQ ID NO:2.

2. The immunogenic composition of claim 1, wherein the nucleic acid molecule comprises a nucleic acid sequence encoding a signal peptide linked to the immunogenic fragment of SEQ ID NO: 2.

3. The immunogenic composition of claim 1 comprising a nucleic acid fragment of SEQ ID NO:1 that comprises at least 50% of the full length of SEQ ID NO:1.

4. The immunogenic composition of claim 1, wherein the nucleic acid molecule is a plasmid.

5. The immunogenic composition of claim 1, wherein the nucleic acid molecule is an expression vector.

6. The immunogenic composition of claim 1, wherein the nucleic acid molecule is incorporated into a viral particle.

7. The immunogenic composition of claim 1 further comprising an adjuvant molecule.

8. The immunogenic composition of claim 7, wherein the adjuvant is IL-12, IL-15, IL-28, or RANTES.

9. A method of inducing an immune response against HBV comprising administering the immunogenic composition of claim 1 to a subject.

* * * * *

SEQUENCE LISTING

```
<160> NUMBER OF SEQ ID NOS: 8

<210> SEQ ID NO 1
<211> LENGTH: 552
<212> TYPE: DNA
<213> ORGANISM: Artificial Sequence
<220> FEATURE:
<223> OTHER INFORMATION: nucleic acid sequence M-core
<220> FEATURE:
<221> NAME/KEY: misc_feature
<222> LOCATION: (1)..(3)
<223> OTHER INFORMATION: n is a, c, g, or t

<400> SEQUENCE: 1
nnngacatcg acccctacaa agaattcggc gccaccgtgg aactgctgag cttcctgccc      60
```

```
agcgacttct tcccctccgt gcgggacctg ctggataccg ccagcgccct gtacagagag    120
gccctggaaa gccccgagca ctgcagccct caccacacag ccctgcggca ggccatcctg    180
tgctggggcg agctgatgac cctggccacc tgggtcggaa gcaacctgga agatcccgcc    240
agccgggacc tggtggtgtc ctacgtgaac accaacatgg gcctgaagat ccggcagctg    300
ctgtggttcc acatctcctg cctgaccttc ggccgggaaa ccgtgctgga atacctggtg    360
tccttcggcg tgtggatcag aaccccccct gcctacagac cccccaacgc ccctatcctg    420
agcaccctgc ccgagacaac cgtggtccgc agacggggca agagcccag aagaagaacc    480 cccagcccta cggcggag atctcagagc cccaggcgga agatcccca gagccgcgag     540 agccagtgct ga                                                       552
```

<210> SEQ ID NO 2
<211> LENGTH: 183
<212> TYPE: PRT
<213> ORGANISM: Artificial Sequence
<220> FEATURE:
<223> OTHER INFORMATION: Amino Acid Sequence of M-Core
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

```
Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Ser Asn Leu Glu Asp Pro Ala
65                  70                  75                  80

Ser Arg Asp Leu Val Val Ser Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 3
<211> LENGTH: 603
<212> TYPE: DNA
<213> ORGANISM: Artificial Sequence
<220> FEATURE:
<223> OTHER INFORMATION: nucleic acid sequence IgE leader - M-Core

<400> SEQUENCE: 3

```
atggactgga cctggattct gttcctggtg gccgctgcca caagggtgca cagcgacatc      60
gaccCCTaca agaattcgg cgccaccgtg aactgctga gcttcctgcc cagcgacttc       120
ttcccctccg tgcgggacct gctggatacc gccagcgccc tgtacagaga ggccctggaa     180
agccccgagc actgcagccc tcaccacaca gccctgcggc aggccatcct gtgctggggc     240
gagctgatga ccctggccac ctgggtcgga agcaacctgg aagatcccgc cagccgggac     300
ctggtggtgt cctacgtgaa caccaacatg ggcctgaaga tccggcagct gctgtggttc     360
cacatctcct gcctgacctt cggccgggaa accgtgctgg aatacctggt gtccttcggc     420
gtgtggatca gaaccccccc tgcctacaga ccccccaacg ccctatcct gagcaccctg      480 cccgagacaa ccgtggtccg cagacggggc agaagcccca agaagaac ccccagccct       540 agacggcgga gatctcagag ccccaggcgg agaagatccc agagccgcga gagccagtgc     600
tga                                                                   603
```

<210> SEQ ID NO 4
<211> LENGTH: 200
<212> TYPE: PRT
<213> ORGANISM: Artificial Sequence
<220> FEATURE:
<223> OTHER INFORMATION: Amino Acid Sequence of IgE leader - M-Core

<400> SEQUENCE: 4

```
Met Asp Trp Thr Trp Ile Leu Phe Leu Val Ala Ala Thr Arg Val
1               5                   10                  15

His Ser Asp Ile Asp Pro Tyr Lys Glu Phe Gly Ala Thr Val Glu Leu
            20                  25                  30

Leu Ser Phe Leu Pro Ser Asp Phe Phe Pro Ser Val Arg Asp Leu Leu
        35                  40                  45

Asp Thr Ala Ser Ala Leu Tyr Arg Glu Ala Leu Glu Ser Pro Glu His
    50                  55                  60

Cys Ser Pro His His Thr Ala Leu Arg Gln Ala Ile Leu Cys Trp Gly
65                  70                  75                  80

Glu Leu Met Thr Leu Ala Thr Trp Val Gly Ser Asn Leu Glu Asp Pro
                85                  90                  95

Ala Ser Arg Asp Leu Val Val Ser Tyr Val Asn Thr Asn Met Gly Leu
            100                 105                 110

Lys Ile Arg Gln Leu Leu Trp Phe His Ile Ser Cys Leu Thr Phe Gly
        115                 120                 125

Arg Glu Thr Val Leu Glu Tyr Leu Val Ser Phe Gly Val Trp Ile Arg
    130                 135                 140

Thr Pro Pro Ala Tyr Arg Pro Pro Asn Ala Pro Ile Leu Ser Thr Leu
145                 150                 155                 160

Pro Glu Thr Thr Val Val Arg Arg Arg Gly Arg Ser Pro Arg Arg Arg
                165                 170                 175

Thr Pro Ser Pro Arg Arg Arg Ser Gln Ser Pro Arg Arg Arg
            180                 185                 190

Ser Gln Ser Arg Glu Ser Gln Cys
        195                 200
```

<210> SEQ ID NO 5
<211> LENGTH: 630
<212> TYPE: DNA
<213> ORGANISM: Artificial Sequence
<220> FEATURE:
<223> OTHER INFORMATION: nucleic acid sequence IgE leader - M-Core + HA
    Tag

<400> SEQUENCE: 5

```
atggactgga cctggattct gttcctggtg gccgctgcca caagggtgca cagcgacatc    60
gaccccctaca agaattcgg cgccaccgtg aactgctga gcttcctgcc cagcgacttc   120
ttcccctccg tgcgggacct gctggatacc gccagcgccc tgtacagaga ggccctggaa   180
agccccgagc actgcagccc tcaccacaca gccctgcggc aggccatcct gtgctggggc   240
gagctgatga ccctggccac ctgggtcgga agcaacctgg aagatcccgc cagccggggac   300
ctggtggtgt cctacgtgaa caccaacatg ggcctgaaga tccggcagct gctgtggttc   360
cacatctcct gcctgacctt cggccgggaa accgtgctgg aatacctggt gtccttcggc   420
gtgtggatca gaaccccccc tgcctacaga ccccccaacg ccctatcct gagcaccctg    480
cccgagacaa ccgtggtccg cagacggggc agaagcccca gaagaagaac ccccagccct   540
agacggcgga gatctcagag ccccaggcgg agaagatccc agagccgcga gagccagtgc   600
taccccctacg acgtgcccga ctacgcctga                                      630
```

<210> SEQ ID NO 6
<211> LENGTH: 209
<212> TYPE: PRT
<213> ORGANISM: Artificial Sequence
<220> FEATURE:
<223> OTHER INFORMATION: Amino Acid Sequence of IgE leader - M-Core + HA Tag

<400> SEQUENCE: 6

```
Met Asp Trp Thr Trp Ile Leu Phe Leu Val Ala Ala Thr Arg Val
1               5                   10                  15

His Ser Asp Ile Asp Pro Tyr Lys Glu Phe Gly Ala Thr Val Glu Leu
            20                  25                  30

Leu Ser Phe Leu Pro Ser Asp Phe Phe Pro Ser Val Arg Asp Leu Leu
        35                  40                  45

Asp Thr Ala Ser Ala Leu Tyr Arg Glu Ala Leu Glu Ser Pro Glu His
    50                  55                  60

Cys Ser Pro His His Thr Ala Leu Arg Gln Ala Ile Leu Cys Trp Gly
65                  70                  75                  80

Glu Leu Met Thr Leu Ala Thr Trp Val Gly Ser Asn Leu Glu Asp Pro
                85                  90                  95

Ala Ser Arg Asp Leu Val Val Ser Tyr Val Asn Thr Asn Met Gly Leu
            100                 105                 110

Lys Ile Arg Gln Leu Leu Trp Phe His Ile Ser Cys Leu Thr Phe Gly
        115                 120                 125

Arg Glu Thr Val Leu Glu Tyr Leu Val Ser Phe Gly Val Trp Ile Arg
    130                 135                 140

Thr Pro Pro Ala Tyr Arg Pro Pro Asn Ala Pro Ile Leu Ser Thr Leu
145                 150                 155                 160

Pro Glu Thr Thr Val Val Arg Arg Arg Gly Arg Ser Pro Arg Arg
                165                 170                 175

Thr Pro Ser Pro Arg Arg Arg Ser Gln Ser Pro Arg Arg Arg
            180                 185                 190

Ser Gln Ser Arg Glu Ser Gln Cys Tyr Pro Tyr Asp Val Pro Asp Tyr
        195                 200                 205

Ala
```

<210> SEQ ID NO 7

```
<211> LENGTH: 18
<212> TYPE: PRT
<213> ORGANISM: Artificial Sequence
<220> FEATURE:
<223> OTHER INFORMATION: IgE leader amino acid sequence

<400> SEQUENCE: 7

Met Asp Trp Thr Trp Ile Leu Phe Leu Val Ala Ala Ala Thr Arg Val
1               5                   10                  15

His Ser

<210> SEQ ID NO 8
<211> LENGTH: 9
<212> TYPE: PRT
<213> ORGANISM: Artificial Sequence
<220> FEATURE:
<223> OTHER INFORMATION: HA Tag amino acid sequence

<400> SEQUENCE: 8

Tyr Pro Tyr Asp Val Pro Asp Tyr Ala
1               5
```